US012426957B2

(12) United States Patent
Kaiser et al.

(10) Patent No.: US 12,426,957 B2
(45) Date of Patent: Sep. 30, 2025

(54) BENDABLE MEDICAL DEVICE WITH MULTIPLE POSITION SENSORS

(71) Applicant: Canon U.S.A., Inc., Melville, NY (US)

(72) Inventors: Christopher Charles Kaiser, Acton, MA (US); Lydia Olson, Swampscott, MA (US); Benedict Shia, Needham, MA (US)

(73) Assignee: Canon U.S.A., Inc., Melville, NY (US)

( * ) Notice: Subject to any disclaimer, the term of this patent is extended or adjusted under 35 U.S.C. 154(b) by 437 days.

(21) Appl. No.: 17/811,036

(22) Filed: Jul. 6, 2022

(65) Prior Publication Data

US 2023/0016761 A1    Jan. 19, 2023

Related U.S. Application Data

(60) Provisional application No. 63/219,301, filed on Jul. 7, 2021.

(51) Int. Cl.
*A61B 34/20* (2016.01)
*A61M 25/01* (2006.01)

(52) U.S. Cl.
CPC ...... *A61B 34/20* (2016.02); *A61B 2034/2059* (2016.02); *A61M 2025/0166* (2013.01)

(58) Field of Classification Search
CPC ........... A61B 34/20; A61B 2034/2059; A61M 2025/0166
See application file for complete search history.

(56) References Cited

U.S. PATENT DOCUMENTS

| 9,144,370 | B2 | 9/2015 | Kato |
| 9,387,048 | B2* | 7/2016 | Donhowe ............... A61B 34/20 |
| 11,007,641 | B2 | 5/2021 | Takagi |
| 11,051,892 | B2 | 7/2021 | Hata |
| 11,103,992 | B2 | 8/2021 | Tanaka |
| 11,278,366 | B2 | 3/2022 | Kose |
| 2007/0135803 | A1 | 6/2007 | Belson |
| 2007/0255145 | A1* | 11/2007 | Smith .................. A61B 5/0215 |
| | | | 600/485 |
| 2012/0289777 | A1* | 11/2012 | Chopra ................ A61B 5/6852 |
| | | | 382/128 |
| 2015/0088161 | A1 | 3/2015 | Hata |
| 2017/0311844 | A1* | 11/2017 | Zhao .................... A61B 1/2676 |
| 2018/0243900 | A1 | 8/2018 | Tanaka |
| 2018/0311006 | A1 | 11/2018 | Kose |
| 2019/0015978 | A1 | 1/2019 | Takagi |

(Continued)

OTHER PUBLICATIONS

Monarch Platform User Manual, Auris Health, Inc., May 2018.
(Continued)

*Primary Examiner* — Kevin T Truong
*Assistant Examiner* — Diana Jones
(74) *Attorney, Agent, or Firm* — Canon U.S.A., Inc. IP Division

(57) ABSTRACT

Some embodiments of a device comprise a tubular flexible body that includes a channel though a longitudinal axis; a first sensor that is located in a distal end of the tubular flexible body; a second sensor that is located in the distal end of the tubular flexible body; and wiring that connects to the first sensor and the second sensor and that extends to a proximal end of the tubular flexible body, wherein a sensed orientation of the first sensor is oriented opposite to a sensed orientation of the second sensor.

22 Claims, 19 Drawing Sheets

(56) References Cited

U.S. PATENT DOCUMENTS

| | | |
|---|---|---|
| 2019/0105468 A1 | 4/2019 | Kato |
| 2019/0192234 A1* | 6/2019 | Gadda .................... A61B 34/37 |
| 2020/0155239 A1* | 5/2020 | West ...................... A61B 34/20 |
| 2021/0308423 A1 | 10/2021 | Kincaid |
| 2021/0386972 A1 | 12/2021 | Chang |
| 2022/0126060 A1 | 4/2022 | Shia |

OTHER PUBLICATIONS

Aurora Features, Northern Digital Inc., downloaded Apr. 2018.
Aurora Tool Design Guide, Northern Digital Inc., Dec. 2005.
Aurora V3.1 User Guide, NDI Europe GmbH, Jan. 2018.
NDI 6D Architect (Verson 3) User Guide, Northern Digital Inc., May 2007.
Aurora Sensors, Northern Digital Inc., downloaded Jul. 20, 2021.
Electromagnetic Tracking, Northern Digital Inc., downloaded Jul. 20, 2021.

* cited by examiner

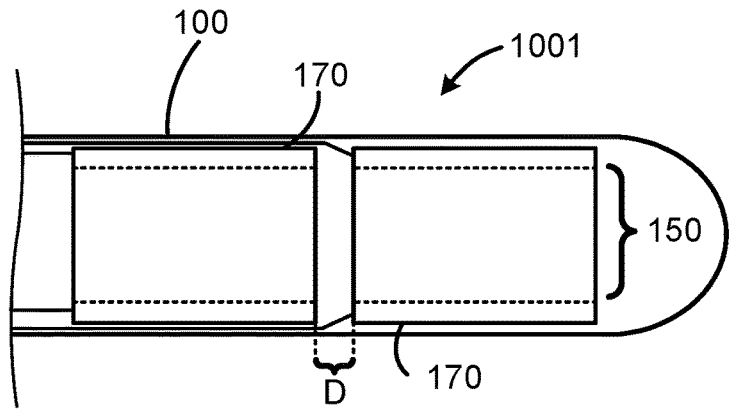
FIG. 4A
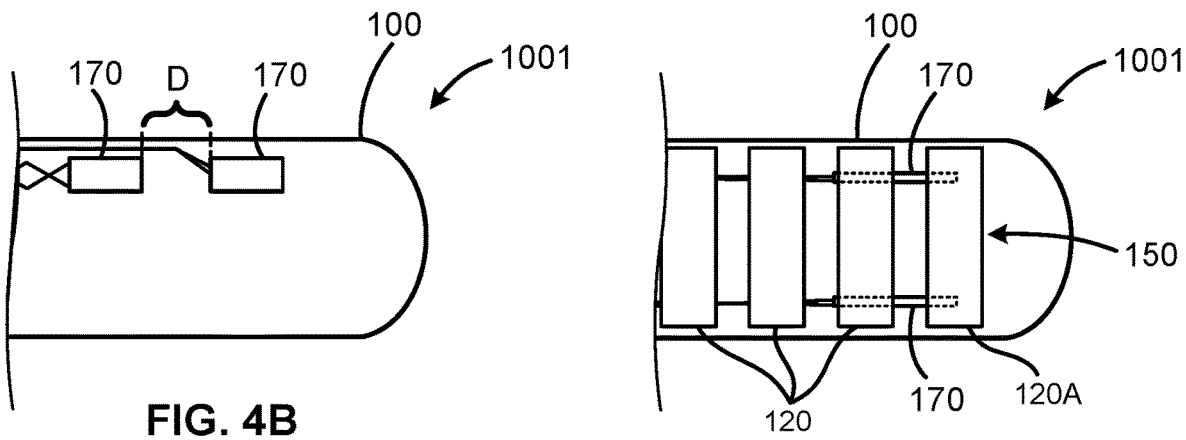
FIG. 4B
FIG. 4C
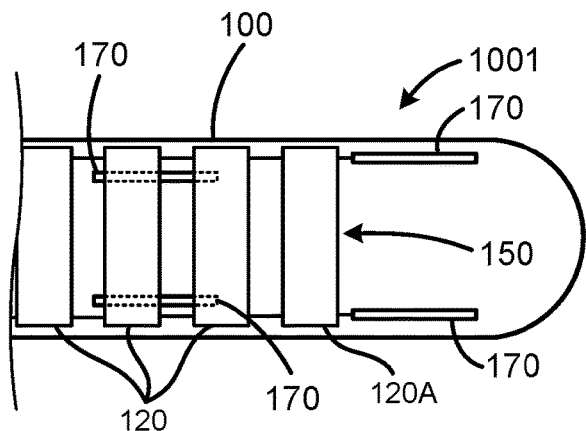
FIG. 4D

BENDABLE MEDICAL DEVICE WITH MULTIPLE POSITION SENSORS

CROSS-REFERENCE TO RELATED APPLICATIONS

This application claims the benefit of U.S. Application No. 63/219,301, which was filed in Jul. 7, 2021.

BACKGROUND

Technical Field

This application generally concerns bendable medical devices and devices, systems, and methods that perform medical procedures using bendable medical devices.

Background

Bendable medical devices can be used to perform medical procedures. For example, bendable optical-imaging devices (e.g., endoscopes, flexible borescopes) enable the imaging of internal tissues, organs, and structures. Also for example, a bendable medical device may be used to reach and biopsy or treat abnormalities in the lung. The bendable medical device, which may include a flexible body, a coil, and a tool (e.g., optical probe), may be navigated through a lumen (e.g., a vessel) or a cavity.

A bendable medical device may include an electromagnetic sensor that allows the location of the device's distal end to be tracked. This allows a physician to know where the distal end is in relationship to the patient's anatomy during a procedure.

SUMMARY

Some embodiments of a device comprise a tubular flexible body that includes a channel though a longitudinal axis; a first sensor that is located in a distal end of the tubular flexible body; a second sensor that is located in the distal end of the tubular flexible body; and wiring that connects to the first sensor and the second sensor and that extends to a proximal end of the tubular flexible body, wherein a sensed orientation of the first sensor is oriented opposite to a sensed orientation of the second sensor.

Some embodiments of a medical system comprise a tubular flexible body that includes a channel though a longitudinal axis; a first sensor that is located in a distal end of the tubular flexible body; a second sensor that is located in the distal end of the tubular flexible body; wiring that connects to the first sensor and the second sensor and that extends to a proximal end of the tubular flexible body; one or more computer-readable storage media; and one or more processors that are in communication with the one or more computer-readable storage media. The one or more processors cooperate with the one or more computer-readable storage media to perform operations that comprise receiving a first signal from the first sensor, wherein the first signal indicates a position and an orientation of the first sensor; receiving a second signal from the second sensor, wherein the second signal indicates a position and an orientation of the second sensor; adjusting the orientation of the second sensor to an orientation that is opposite to the orientation of the second sensor, thereby generating an adjusted orientation of the second sensor; and calculating a position and an orientation of the distal end of the tubular flexible body based on the position and the orientation of the first sensor and on the position and the adjusted orientation of the second sensor.

Some embodiments of a device comprise one or more computer-readable storage media and one or more processors that are in communication with the one or more computer-readable storage media. The one or more processors cooperate with the one or more computer-readable storage media to perform operations that comprise receiving a first signal from a first sensor that is located in a distal end of a tubular flexible body, wherein the first signal indicates a position and an orientation of the first sensor; receiving a second signal from a second sensor that is located in the distal end of the tubular flexible body, wherein the second signal indicates a position and an orientation of the second sensor; adjusting the orientation of the second sensor to an orientation that is opposite to the orientation of the second sensor, thereby generating an adjusted orientation of the second sensor; and calculating a position and an orientation of the distal end of the tubular flexible body based on the position and the orientation of the first sensor and on the position and the adjusted orientation of the second sensor.

BRIEF DESCRIPTION OF THE DRAWINGS

FIG. 4A illustrates an example embodiment of a distal end that includes two sensors.

FIG. 4B illustrates an example embodiment of a distal end that includes two sensors.

FIG. 4C illustrates an example embodiment of a distal end that includes two sensors.

FIG. 4D illustrates an example embodiment of a distal end that includes four sensors.

DESCRIPTION

Figure 1A:
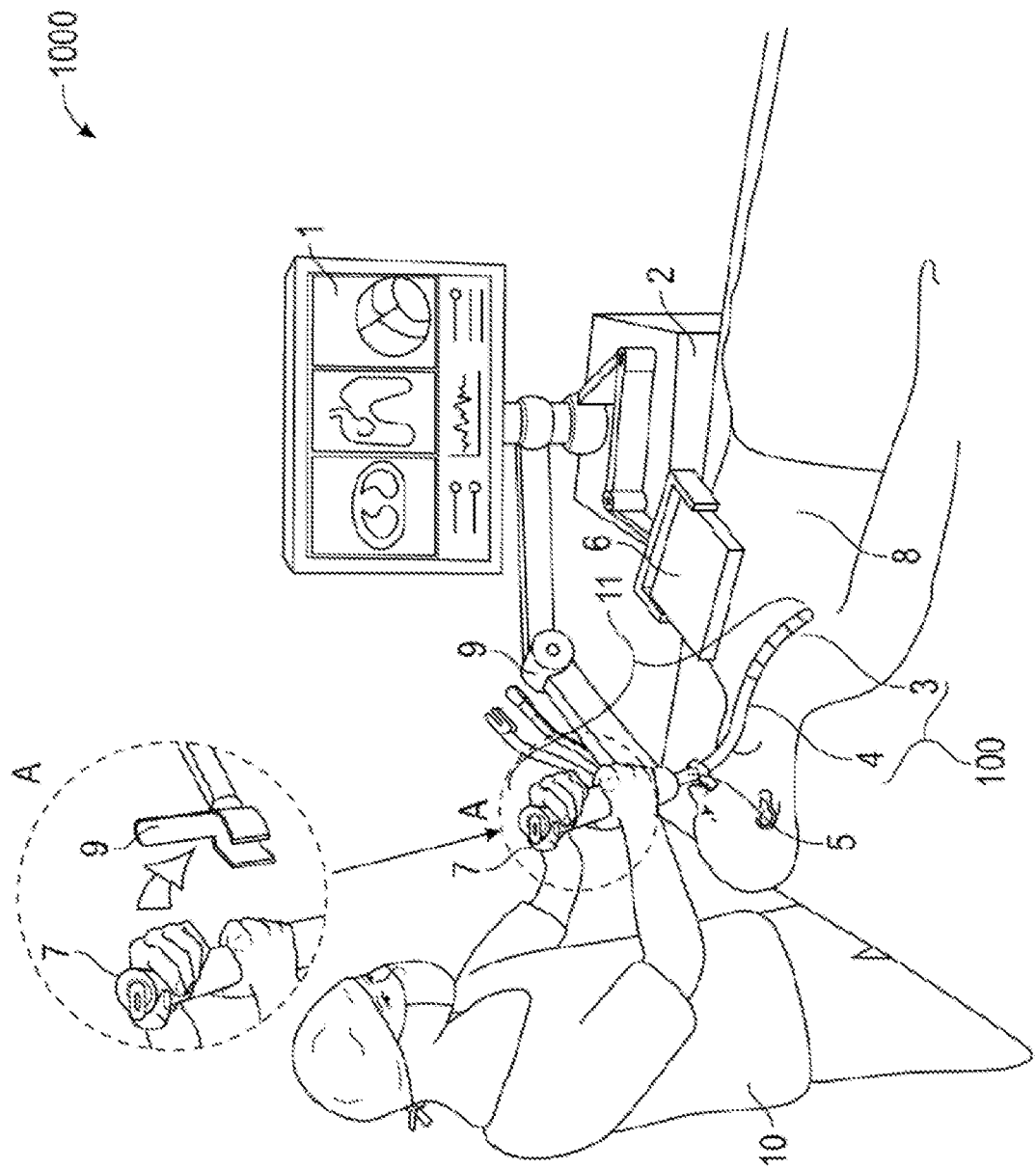
FIG. 1A illustrates an example embodiment of a medical system that includes a steerable medical device in an applicable medical environment thereof.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments.

Also, as used herein, the conjunction "or" generally refers to an inclusive "or," although "or" may refer to an exclusive "or" if expressly indicated or if the context indicates that the "or" must be an exclusive "or." Furthermore, as used herein, the terms "first," "second," and so on, do not necessarily denote any ordinal, sequential, or priority relation and may be used to more clearly distinguish one member, operation, element, group, collection, set, etc. from another without expressing any ordinal, sequential, or priority relation.

Additionally, in this description and the drawings, an alphabetic suffix on a reference number may be used to indicate a specific instance of the feature identified by the reference numeral. For example, the sensors in a group of sensors may be identified with the reference numeral 170 when a particular sensor is not being distinguished. However, 170A may be used to identify a specific sensor when the specific sensor is being distinguished from the rest of the sensors 170.

FIG. 1A, FIG. 1B, and FIGS. 2A-2C describe the structure and functionality of exemplary bendable medical devices that can be used with the systems and methods described herein. The bendable medical device of the robotic medical system 1000 can include a continuum or multi-segment robot configured to form a continuously curved geometry by actuating one or more bending sections of a steerable section 3 of the bendable medical device.

A robotic medical system will be described by referring to FIG. 1A and FIG. 1B. FIG. 1A illustrates an example embodiment of a medical system 1000 in a medical environment, such as an operating room. The medical system 1000 includes at least a navigation system 1, a controller system 2, a field generator 6, and a steerable instrument 11.

The medical system 1000 makes use of the steerable instrument 11 (steerable medical device) to treat a patient 8 under interactive commands of a user (e.g., a physician) 10. The steerable instrument 11 includes a connector assembly 5, an actuation unit 7, and a catheter sheath 100.

The steerable instrument 11 is an example of a bendable medical device, and some embodiments of the medical system 1000 (e.g., non-robotic embodiments of the medical system 1000) include a different bendable medical device. Thus, while the following description refers to a steerable instrument 11 when describing some embodiments, other embodiments include a different bendable medical device (e.g., an endoscope, a flexible borescope) in addition to, or in alternative to, the steerable instrument 11. Also, the catheter sheath 100 is an example of a tubular flexible body (tubular bendable body), and some bendable medical devices include a different tubular flexible body. Accordingly, while the following description refers to a catheter sheath 100 when describing some embodiments, other embodiments include a different tubular flexible body in addition to, or in alternative to, the catheter sheath 100.

The steerable catheter sheath 100 includes a multi-segment distal steerable section 3 and a single-segment proximal section 4. The proximal section 4 is connected to the actuation unit 7 via the connector assembly 5. The actuation unit 7 is configured to be detachably mounted to a robotic platform (support platform) 9, as shown in detail on the inset A of FIG. 1A.

The steerable instrument 11 can be configured for a number of medical applications and/or industrial applications. Under medical applications, the steerable instrument 11 can be configured as a robotic endoscope, as a steerable catheter, or as a surgical introducer sheath or sleeve that uses principles of kinematic (robotic) navigation for guiding a medical tool through tortuous bodily lumens, for example. Robotic endoscopes can be used for a variety of different diagnostic and interventional procedures including, but not limited to, colonoscopy, bronchoscopy, laparoscopy, video endoscopy, etc. In the case of a video endoscope, the steerable instrument 11 would be configured with a miniature video camera, such as a CCD or CMOS camera, positioned at the distal portion of the steerable section 3, as well as electronic cabling and illumination optics (an optical fiber) extending along the tool channel.

Figure 1B:
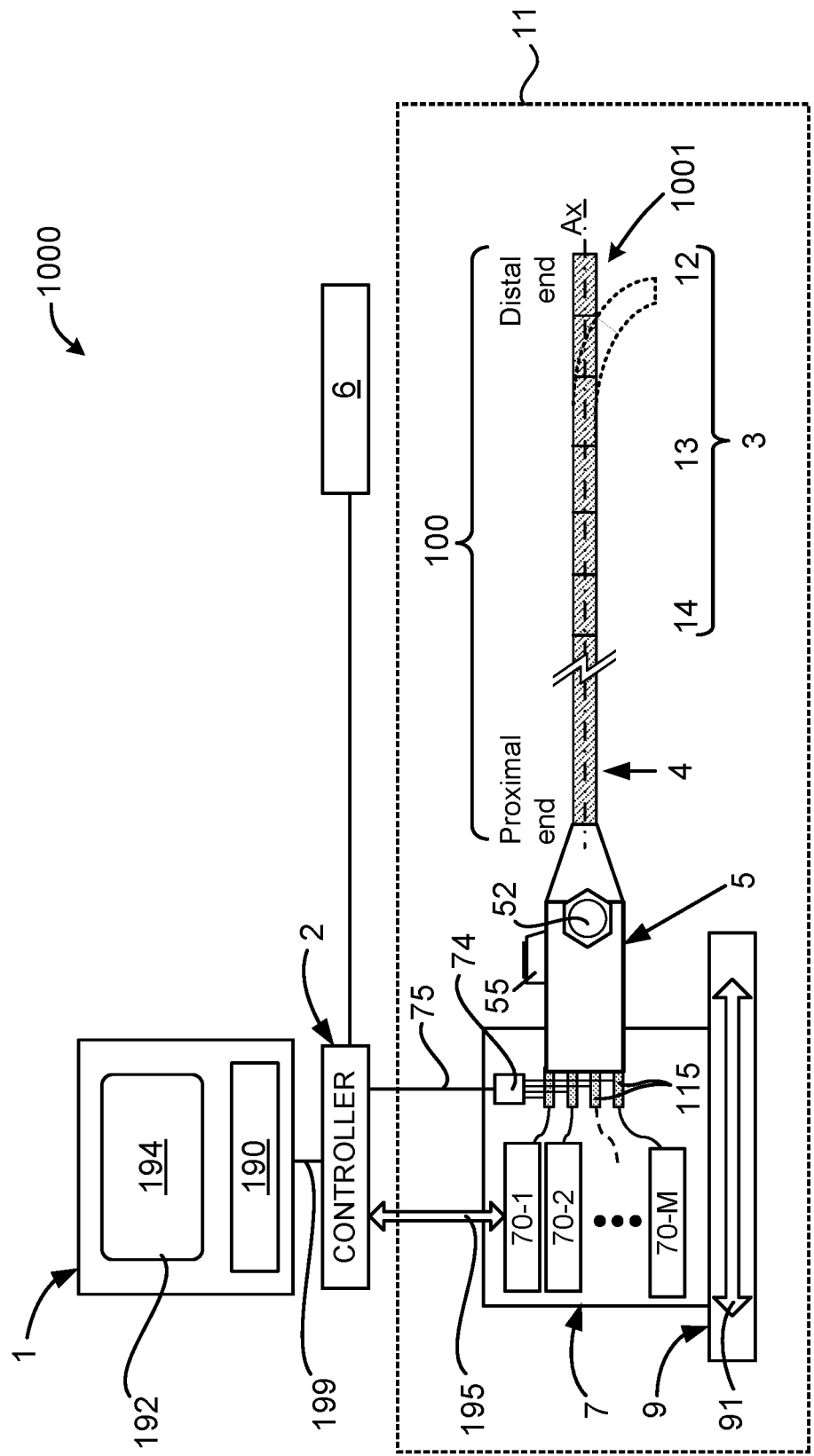
FIG. 1B illustrates an example embodiment of the medical system in FIG. 1 in block diagram form.

FIG. 1B illustrates an example embodiment of the medical system 1000 in block diagram form. The catheter sheath 100 has a proximal non-steerable section 4 and a distal steerable section 3 made of multiple bending segments (e.g., bending segments 14, 13, 12) which are arranged lengthwise along a longitudinal axis (Ax). At least one central lumen or tool channel extends along the length of the catheter sheath 100 and through part of the connector assembly 5. In some embodiments, the steerable instrument 11 is controlled by a robotic controller system 2 via the actuation unit 7; the actuation unit 7 is a handheld controller (handle) connected to the proximal section 4 of the catheter sheath 100 by the connector assembly 5. The actuation unit 7 can include any applicable force-generating device and a mechanical element respectively used to generate and transmit sufficient actuating force for bending at least one bending segment of the steerable section 3. In that regard, the actuation unit 7 may include any device capable of generating and transmitting an actuating force including, for example, a mechanical force, a hydraulic force, a magnetic force, or a pneumatic force. The support platform 9 may include, for example, a robotic arm and a linear stage 91, which serves to guide the steerable instrument 11 (control unit 7, connector assembly 5, and catheter sheath 100) in a moving direction (typically linear movement) for insertion and/or retraction of the catheter sheath 100 with respect to the patient 8.

The controller system 2 generally includes electronic components, such as a proportional integral derivative (PID) controller and/or a digital signal processor (DSP) device along with suitable software, firmware and peripheral hardware, which are generally known to persons having ordinary skill in the art. The controller system 2 can be part of, or is connected to, the navigation system 1 (e.g., a computer or system console). The navigation system 1 includes the necessary software (computer-executable code, programs, and applications) executable by one or more processors 190, according to a user's interactions with the system 1000 via a user interface 194, to control the steerable instrument 11. The operations of the one or more processors 190 may be implemented by loading and executing a program or may be implemented by a dedicated circuit (e.g., FPGA, ASIC). The user interface 194 may include, for example, a display device 192 (e.g., LCD, LED, or OLED display), which may include a graphical user interface (GUI), a pointing device and keyboard (not shown), or a touchscreen.

The navigation system 1, the controller system 2, and the actuation unit 7 are operably connected to each other by a network connection or a cable bundle 199 and a data bus system 195. Among other functions, the navigation system 1 can provide a surgeon or other user with a GUI and other information displayed in the image display device 192, so that the user can interact with and remotely operate the steerable instrument 11. For example, the navigation system 1 can display information that indicates the position and orientation of the distal end 1001 of the catheter sheath 100 on the image display device 192, and the information may be presented in the form of images, graphics, or text.

The controller system 2 is configured to control the actuation unit 7, which includes a plurality of actuating motors (or actuators) 70-1, 70-2 . . . , 70-M. The number of actuators or motors will depend on the design of the actuation unit 7, and it can include a single (one) actuator or motor that can actuate all driving wires independently, or it could include a number of actuators or motors, for example a number equal to a number of driving wires 115 so that each actuator or motor can individually actuate a respective driving wire 115.

The controller system 2 may also include or be connected to one or more actuation-control sensors 74. The actuation-control sensors 74 can include a strain sensor and/or a position sensor that are configured to detect and/or measure compressive or tensile forces (actuating forces) exerted on the driving wires 115 to bend one or more of the segments 12, 13, and 14. The actuation-control sensors 74 may output a signal 75 corresponding to an amount of compressive or tensile force (an amount of strain) being applied to a driving wire 115 at any given point in time. The signals 75 from the actuation-control sensors 74 (strain sensor and/or position sensor) for each driving wire are fed into the controller system 2 to control each actuator (or driving wire 115) individually. In this manner, each driving wire 115 can be actively controlled, by a feedback loop, to implement appropriate shaft guidance for navigating the steerable section 3 through intraluminal tortuous paths of a patient's anatomy.

Figure 2A:
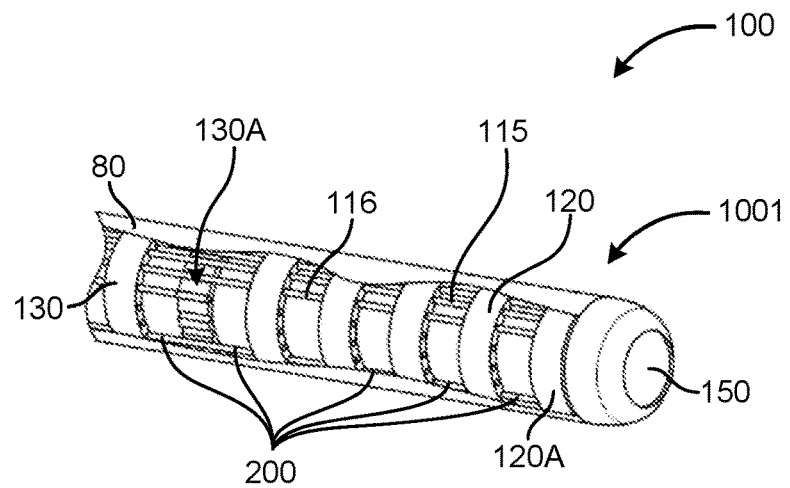
FIG. 2A and FIG. 2B illustrate structural details of a steerable catheter sheath with a central lumen extrusion and a plurality of guide rings arranged on the central lumen extrusion.
Figure 2B:
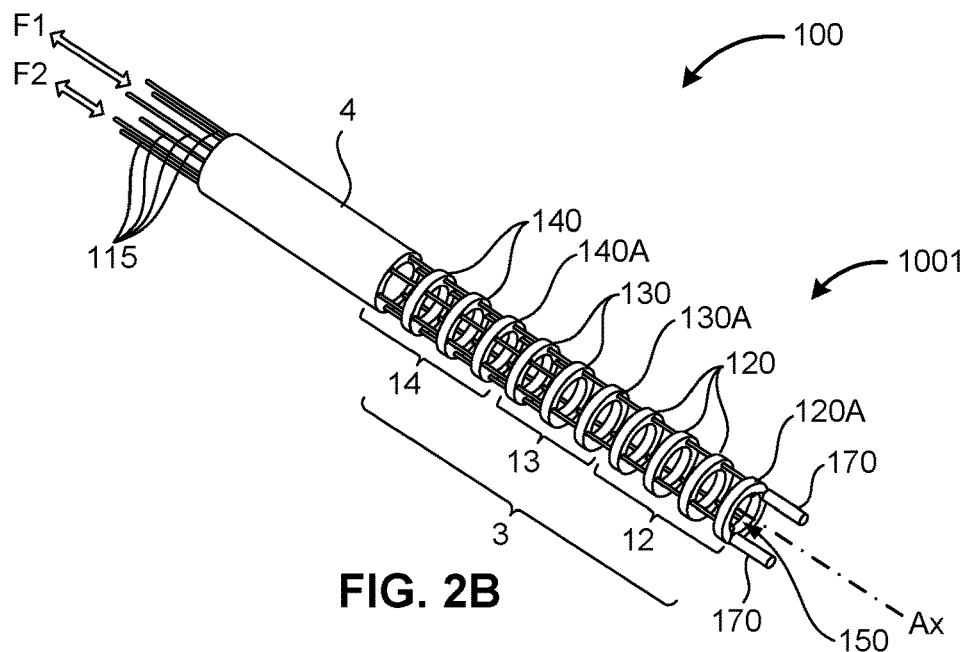

FIG. 2A and FIG. 2B illustrate additional details of the catheter sheath 100, according to an example embodiment. FIG. 2A is a three-dimensional partially cutaway view and FIG. 2B is a perspective view of the catheter sheath 100, which is composed of a non-steerable proximal section 4 and a steerable distal section 3. The steerable section 3 incudes a plurality of bending segments, including a proximal bending segment 14, a middle bending segment 13, and a distal bending segment 12. As shown in FIG. 2B, each bending segment is formed of two or more rings (a plurality of rings) cooperatively arranged in a lengthwise direction to form a tubular structure. As shown in FIG. 2A, the tubular structure also includes an outer jacket 80 and a central lumen extrusion 200. The central lumen extrusion 200 includes an inner liner reinforced by a reinforcing structure. The inner liner has an inner surface which defines a central lumen or tool channel 150 and has an outer surface onto which a plurality of rings are arranged. To improve the navigation process, it can be advantageous to reinforce the inner liner of the central lumen or tool channel 150. The rings include a plurality of wire conduits (secondary lumens) through which driving wires 115 and/or support wires 116 are passed. The driving wires 115 are moved by an actuating force to bend one or more segments of the steerable section 3; the support wires 116 are not actuated.

FIG. 2B illustrates an example of the catheter sheath 100 without the central lumen extrusion 200 and without the outer jacket 80. As shown in FIG. 2B, the plurality of driving wires 115 pass through the proximal section 4, advance through wire conduits of wire-guiding rings 140 of the proximal bending segment 14, pass through wire conduits of wire-guiding rings 130 of the middle bending segment 13, and pass through wire conduits of wire-guiding rings 120 of the distal bending segment 12. Each bending segment of the steerable section is actuated by a set of antagonistic driving wires 115, which operate by a pulling or pushing force (an actuating force) to bend each bending segment independently of each other. Forces F1 and F2 of different magnitude can be applied in the lengthwise direction to cause separate driving wires to bend the various bending segments in desired directions. A combination of forces F1 and F2 can also be applied to bend a given bending segment in additional directions. To that end, a first set of driving wires 115 may be anchored at an anchor ring 120A at the distal end of the distal bending segment 12, a second set of driving wires 115 may be anchored at an anchor ring 130A of the middle bending segment 13, and at a third set of driving wires 115 may be anchored at an anchor ring 140A of the proximal bending segment 14.

According to one embodiment, three driving wires 115 may be used to actuate each bending section. In that case, the distal ends 1001 of the driving wires 115 in the first set of driving wires can be anchored to the anchor ring 120A, the second set of driving wires can be anchored to the anchor ring 130A, and the third set of driving wires can be anchored to the anchor ring 140A. In such example, nine driving wires 115 will pass through the proximal section 4 of the steerable sheath. At each anchor member, it may be advantageous to arrange (to anchor) the driving wires 115 equidistantly around the circumference of the anchor member at strategic locations so as to actuate each bending segment independently in a desired direction. For example, the driving wires 115 can be anchored at equal intervals on the anchor member such that, when each bending segment is actuated by three wires, the driving wires would be anchored at 120-degree intervals to be able to actuate each bending segment in substantially any direction (any angle with respect to lumen axis Ax).

As shown in FIG. 2A and FIG. 2B, in the catheter sheath, each bending segment 12, 13, and 14 includes a plurality of ring-shaped wire-guiding members (wire-guiding rings), while the proximal non-steerable section 4 is a single-piece elongated tubular component. Here, the tubular-shaped proximal section 4 and the central lumen extrusion 200 can be made of similar biocompatible polymer materials, such as polyether block amide copolymer (e.g., Pebax® brand produced by Arkema), which is a well-known polymer used in the fabrication of catheter shafts. Other medical-grade thermoplastic polyurethane (TPU) and thermoplastic elastomer (TPE) materials can also be used as tubing-extrusion materials for medical catheter and endoscope devices that demand precision and consistency. Furthermore, other commonly known catheter-tubing materials may be used, including PVC, HDPE, Polyurethane, Nylon, FEP, PFA, ETFE, PTFE (liners), PEEK, TPE, Grilamid® lubricious films, and many others.

Each wire-guiding member (each wire-guiding ring) 120, 130, and 140 has a plurality of wire conduits (or thru-holes) along the wall of the wire-guiding member. The thru-holes serve as conduits through which wires are guided along the wall of the tubular shaft. Again, the wire conduits could also be formed on the outer surface of each wire-guiding member. The number of wire conduits in each wire-guiding member depends on the bending section in which the wire-guiding member is arranged. The distal bending segment 12 includes a plurality of wire-guiding rings 120; the middle bending segment 13 includes a plurality of wire-guiding rings 130; and the proximal bending segment 14 includes a plurality of wire-guiding rings 140. The distal bending segment 12 is joined to the middle bending segment 13 by an anchor ring 130A, and the middle bending segment 13 is connected to the proximal bending segment 14 by an anchor ring 140A. The proximal section 4 is a non-steerable section, but it does include a plurality of wire conduits extending through the wall (or on the outer surface of the wall). Here, it should be noted that wire conduits are not limited to thru-holes or conduits within the wall itself. In some embodiments, the wire conduits can be formed on the outer surface or the inner surface of the individual wire-guiding rings. Moreover, at least some wire-guiding rings can be formed without thru-holes or conduits.

Figure 2C:
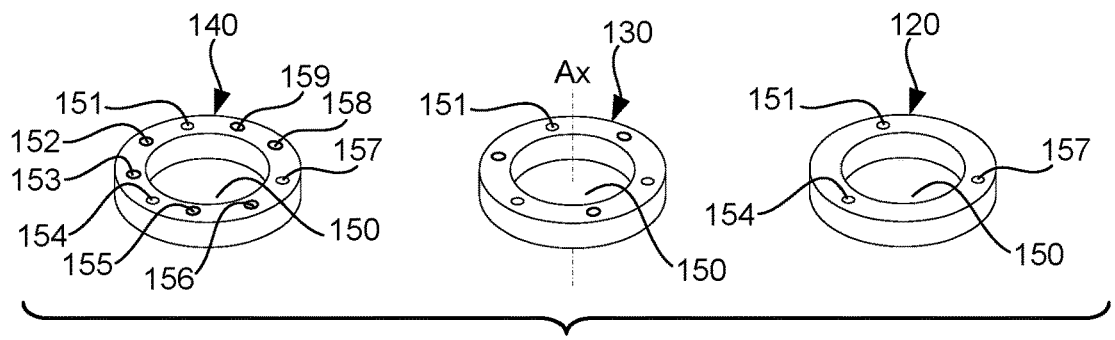
FIG. 2C shows examples of guide rings having wire conduits (wire-guiding conduits) for wires.

FIG. 2C shows example embodiments of annular-shaped wire-guiding rings (guide rings) having a central opening or tool channel 150 and secondary lumens or wire conduits (151, 152, 153, 154, 155, 156, 157, 158, 159) formed in the wall of the wire-guiding rings surrounding the tool channel 150. The outer surface and the inner surface of each wire-guiding ring is shown as circular for ease of illustration, but some embodiments are not limited thereto. For example, the outer surface and the inner surface of each wire-guiding ring can have a substantially symmetric and closed polygonal shape, such as a hexagon, octagon, etc.

FIG. 2C shows one wire-guiding ring 120, one wire-guiding ring 130, and one wire-guiding ring 140. The wire-guiding ring 120 includes three wire conduits (wire-guiding conduits) (151, 154, 157); the wire-guiding ring 130 includes six wire conduits (152, 153, 155, 156, 158, 159); and the wire-guiding ring 140 includes nine wire conduits (151, 152, 153, 154, 155, 156, 157, 158 and 159). In this embodiment, nine driving wires 115 can be arranged through the tubular wall in the proximal section 4. Then, the driving wires continue through the wire conduits of the proximal bending segment 14, and are anchored to an anchor member for each bending segment. The anchoring rings 120A, 130A and 140A are of substantially similar structure as the corresponding wire-guiding rings 120, 130, and 140, respectively. All wire-guiding members and anchoring members include a central opening or tool channel 150, and have a predetermined number of thru-holes (wire-guiding conduits or secondary lumens) arranged around the tool channel 150 and substantially parallel to, and equidistant from, the instrument axis Ax.

In referring to FIG. 2A-FIG. 2C, it should be understood that not all thru-holes must be used for driving wires 115. At least some of the thru-holes may be used to pass an electrical cable (e.g., wiring for sensors 170), some through holes may be empty, and some may have support wires that are not driving wires 115. That is, according to some embodiments, the thru-holes of each wire-guiding ring can have several uses. For example, some thru-holes may contain a control wire (driving wire), some may contain a support wire that transmits no force, some are left empty, some may pass an optical fiber, some may have an electrical cable, and some may have an electronic component, such as a load cell or sensor. The rings for the steerable section 3 can be made of biocompatible thermoplastic polymer similar to that used for the central lumen extrusion or the proximal section 4.

Referring back to FIG. 1A and FIG. 1B, the handle or connector assembly 5 provides an electromechanical interface between the proximal section 4 and the actuators in the actuation unit 7. For example, the connector assembly 5 may provide mechanical, electrical, and/or optical connections, and other data/digital connections for interfacing the steerable instrument 11 with the controller system 2 and the navigation system 1. The handle or connector assembly 5 may also provide an access port 55, which can be used by a surgeon or other operator to insert instruments, imaging devices, or other end effectors through the tool channel 150. For example, the access port 55 can be used to insert small instruments, such as small forceps, needles, or electrocautery instruments and the like. In addition, the connector assembly 5 may include one or more dials or control wheels 52 for manual control (bending or steering) of at least one segment of the steerable section 3. In some embodiments, the steerable section 3 may include more than one tool channel 150, where at least one of those channels can be used for passing liquid and/or gaseous fluids, and another channel can be used for passing tools or imaging devices.

In operation, the navigation system 1 and the controller system 2 are communicatively-coupled via the data bus 199 to transmit and receive data to and from each other. The navigation system 1 is also connected to, and communicates with, external equipment, such as a computed tomography (CT) scanner, a fluoroscope imager, an image server (not shown in FIG. 1A), etc., which are external of the medical system 1000. The image server may include, but is not limited to, a DICOM™ server connected to a PACS (Picture Archiving and Communication System) or medical imaging system, which may include, but is not limited to, one or more of a CT scanner, a magnetic resonance imaging (MRI) scanner, or a fluoroscope, etc. The navigation system 1 processes data provided by the controller system 2, data provided by images stored on the image server, or data provided by images from the CT scanner or the fluoroscope. The navigation system 1 displays images and other medical information in an image display device 192 to aid the user 10 in performing a medical procedure. For example, as noted above, the navigation system 1 can display information that indicates the position and orientation of the distal end 1001 of the catheter sheath 100.

For a medical procedure where the steerable instrument 11 will be used, medical images (e.g., from the CT scanner) are pre-operatively provided to the navigation system 1. With the navigation system 1, a clinical user creates an anatomical computer model from the images. In some embodiments of FIG. 1A, the anatomy can be the lung airways of the patient 8. From chest images received from the CT scanner or PACS system, the clinical user can segment the lung airways for clinical treatments, such as a biopsy. After the navigation system 1 generates a map of the lung airways, the user can also use the navigation software system to create a plan to access a lesion for the biopsy. The plan includes the target lesion and a trajectory (navigation path) through the airways to insert the steerable section 3 (steerable sheath) of the steerable instrument 11.

The controller system 2 includes firmware, control circuitry, and peripheral hardware to control the steerable instrument 11, the insertion unit 9, and the field generator 6 (e.g., an electromagnetic (EM) field generator). The controller system 2 is communicatively coupled with the actuation unit 7, the insertion unit 9, the field generator 6, and a man-machine interface (e.g., a gamepad controller not shown in FIG. 1A-FIG. 1B). In this manner, the controller system 2, in coordination with the navigation system 1, controls the overall functions of the steerable instrument 11 and the insertion unit 9.

The actuation unit 7 is configured to bend one or more of the proximal bending segment 14, the middle bending segment 13, and the distal segment 12 via the connector assembly 5 according to commands from the controller system 2, and based on the navigation plan provided by navigation system 1.

According to some embodiments, either during insertion or retraction of the steerable instrument 11, the controller system 2 may control the linear stage 91 of insertion unit 9 to move the steerable section 3 along the center line of a lumen (e.g., an airway) in a desired trajectory followed by active control of the bending segments. This is similar to known shaft-guidance techniques used to control robotic guided catheters or endoscopes with the goal of forcing the flexible shaft of the sheath to keep to a desired trajectory. In one example, when using the navigation system 1, the steerable instrument 11 is robotically controlled to advance the sheath through a lumen while the actuation-control sensors 74 measure the actuation force, insertion depth, the angulations of user-controlled steerable segments, etc., to obtain trajectory information. The trajectory information is stored in a memory of the system and continuously updated. After a short advance in insertion or retraction distance, the shape of the steerable section 3 is changed (e.g., corrected) by adjusting (actuating) one or more of the bending segments in such a way that the new shape closely matches the desired trajectory. This process is repeated until a target area is reached. The same process can be applied when the steerable instrument is controlled to withdraw the steerable section 3 from the patient.

The steerable instrument 11 also includes two or more sensors 170. In some embodiments, the two or more sensors 170 are electromagnetic (EM) sensors. And, in some embodiments, the sensors 170 are five-degree-of-freedom or six-degree-of-freedom sensors. Also, in some embodiments, the two or more sensors 170 are fixed relative to each other at or near the distal end 1001 (e.g., tip) of the catheter sheath 100 or at or near the distal end of the steerable section 3 (e.g., the distal end of the distal bending segment 12), which may also be the distal end 1001 of the catheter sheath 100.

The controller system 2 communicates with the sensors 170 to determine the positions or orientations of the sensors 170. The sensors 170 detect a field that is generated by the field generator 6 and send signals that are based on the detected field to the controller system 2 or to the navigation system 1, and the controller system 2 or the navigation system 1 uses the signals to calculate the positions or orientations of the sensors 170. And, based on the positions or orientations of the sensors 170, the controller system 2 or navigation system 1 determines the positions or orientations of the distal end 1001 of the catheter sheath 100, which may also be the distal end of the steerable section 3 (e.g., the distal end of the distal bending segment 12).

In embodiments in which the relative positions and orientations of the sensors 170 are fixed, and thus the distance (or distances) between the sensors 170 is fixed, the sensors 170 move together in unison. Consequently, if there is a discrepancy between the sensors' relative positions or orientations, this discrepancy can be attributed to measurement error. Additionally, locating the sensors 170 at the distal end 1001 enables the user to know when the distal end 1001 has navigated to an area of interest in a lumen, cavity, or other structure.

In FIG. 2B, the sensors 170 are located on the distal side of the distal bending segment 12. However, in some embodiments, the sensors 170 are at least partially positioned in the tool channel 150 (e.g., at least partially within an internal radius of the wire-guiding rings 120, 130, 140). Also, the sensors 170 may be positioned outside of the outer radius of the wire-guiding rings 120, 130, 140 or be embedded in one or more wire-guiding rings. The positions of the sensors 170 that are described herein are examples, and, in some embodiments, the positions of the sensors 170 are different from the positions that are described herein. Accordingly, the positions of the sensors 170 may be adapted for the requirements of various applications.

Also, various wiring configurations may be used for the wires of the sensors 170. For example, the wires of the sensors 170 may pass through the tool channel 150; may pass though one or more wire conduits (or thru-holes); may be embedded in the outer jacket 80; may be embedded in the central lumen extrusion 200; may be located between the central lumen extrusion 200 and the wire-guiding rings 120, 130, 140; or may be located between the outer jacket 80 and the wire-guiding rings 120, 130, 140. And each of the wires may follow a different route through the steerable instrument 11.

Figure 3A:
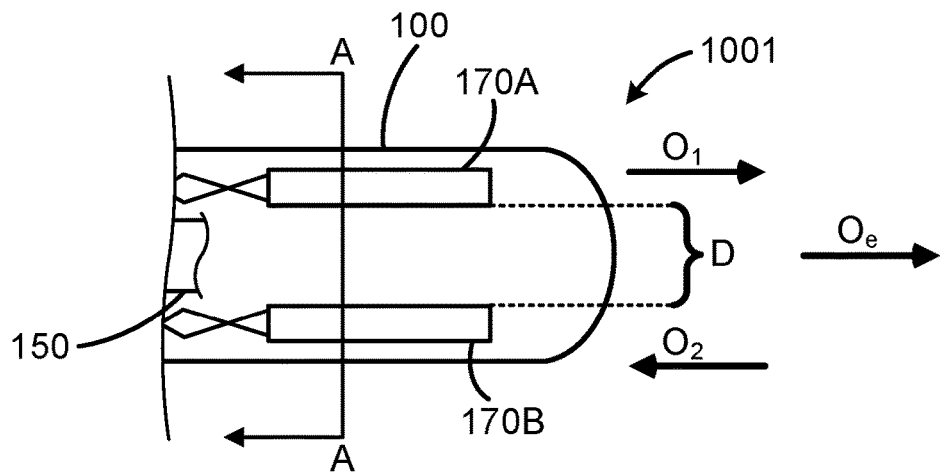
FIG. 3A illustrates an example embodiment of a distal end, of a bendable medical device, that includes two sensors.

FIG. 3A illustrates an example embodiment of a distal end 1001 of a catheter sheath 100. FIG. 3A shows a cutaway view of the distal end 1001, and the distal end 1001 includes two sensors 170. In some embodiments, the distance D between the two sensors is 5 mm or less, although the distance is different in other embodiments. For example, in some embodiments, the distance D is 5 mm or less and is 2 mm or more ($2 \leq D \leq 5$), the distance D is 7 mm or less and is 1 mm or more ($1 \leq D \leq 7$), the distance D is 4 mm or less and is 3 mm or more ($3 \leq D \leq 4$), the distance D is 10 mm or less and is 3 mm or more ($3 \leq D \leq 10$), or the distance D is 20 mm or less and is 2 mm or more ($2 \leq D \leq 20$).

Figure 3B:
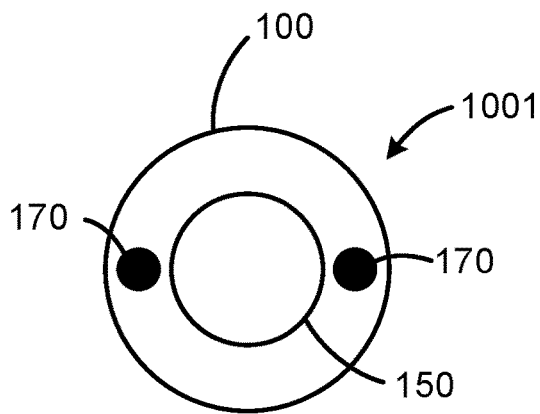
FIG. 3B illustrates a cutaway view of the distal end in FIG. 3A taken from line A-A.
Figure 3C:
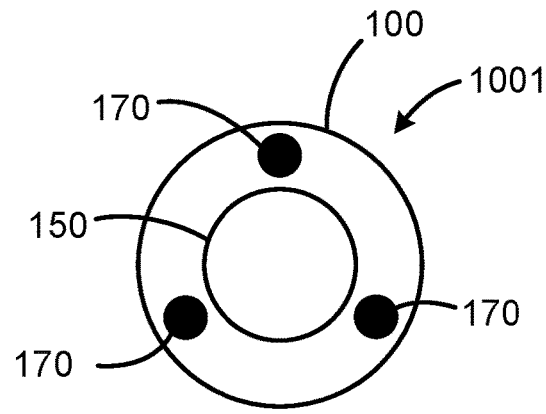
FIG. 3C illustrates a cutaway view of an example embodiment of a distal end that includes three sensors.

FIG. 3B illustrates a cutaway view of the distal end 1001 in FIG. 3A taken from line A-A. In FIG. 3B, the two sensors 170 are located on opposite sides of the catheter sheath 100. Also, a tool channel 150 is visible between the two sensors 170. Furthermore, in some embodiments of the catheter sheath 100, the distal end 1001 includes three or more sensors 170. For example, FIG. 3C illustrates a cutaway view of an example embodiment of a distal end 1001 that includes three sensors 170. In FIG. 3C, the sensors are evenly spaced around the perimeter of the distal end 1001.

In some embodiments, one of the sensors 170 is wired such that its detected orientation is opposite to the other sensor 170. For example, in some embodiments, pins $P_1$ and $P_2$ of one sensor 170 are wired +/−, while in the other sensor 170 pins $P_1$ and $P_2$ are wired −/+. Because of this wiring configuration, the controller system 2 or navigation system 1 detects that the sensors 170 are oriented (e.g., pointing) in opposite directions. For example, in FIG. 3A, a first sensor 170A is wired such that the controller system 2 or navigation system 1 detects that the first sensor 170A is oriented in a first direction $O_1$, and a second sensor 170B is wired such that the controller system 2 or navigation system 1 detects that the second sensor 170B is oriented in a second direction $O_2$ that is opposite to the first direction $O_1$ and opposite to the orientation $O_e$ of the distal end 1001.

Figure 3D:
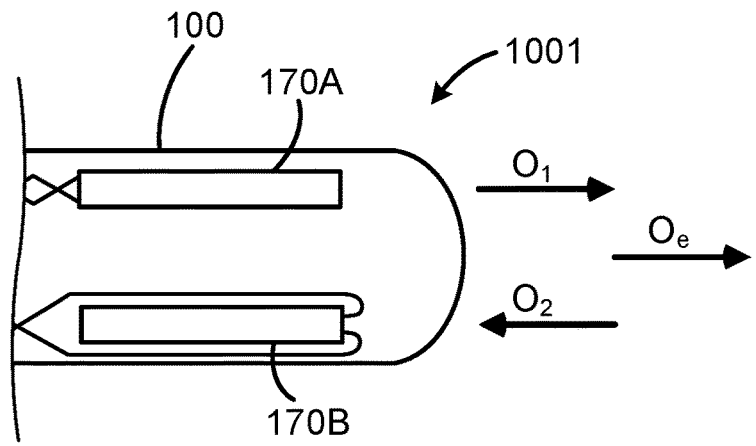
FIG. 3D illustrates an example embodiment of a distal end that includes two sensors that are physically oriented opposite to each other.

However, in some embodiments the sensors 170 are physically oriented opposite to each other. For example, FIG. 3D illustrates an example embodiment of a distal end 1001 that includes two sensors 170 that are physically oriented opposite to each other. And, because of this physical configuration, the controller system 2 or navigation system 1 detects that the sensors 170 are oriented in opposite directions. For example, in FIG. 3D, a first sensor 170A is physically oriented such that the controller system 2 or navigation system 1 detects that the first sensor 170A is oriented in a first direction $O_1$, and a second sensor 170B is physically oriented such that the controller system 2 or navigation system 1 detects that the second sensor 170B is oriented in a second direction $O_2$ that is opposite to the first direction $O_1$ and that is opposite to the orientation $O_e$ of the distal end 1001.

Also, the controller system 2 or navigation system 1 can adjust (e.g., modify, change, transform) the reading of the sensor 170 that is wired or oriented such that the orientation of the sensor 170, as read by the controller system 2 or navigation system 1, is opposite to the orientation of the distal end 1001 of catheter sheath 100. For example, the controller system 2 or navigation system 1 can adjust the second direction $O_2$ to produce an adjusted second direction $O_{2'}$ that is oriented in the opposite direction of the second direction $O_2$. Thus, assuming that the first direction $O_1$ is opposite to the second direction $O_2$, the adjusted second direction $O_{2'}$ would be identical to the first direction $O_1$.

Also, the two sensors 170 may have other configurations. For example, FIG. 4A illustrates an example embodiment of a distal end 1001 that includes two sensors 170. FIG. 4A shows a cutaway view of the distal end 1001. The distal end 1001 includes two sensors 170 that are aligned along their longitudinal axes, and each of the sensors 170 includes a tool channel 150 through its center. Also, in this embodiment, one of the sensors 170 is wired such that its detected orientation is opposite to the other sensor 170. However, as noted above, in some embodiments the sensors 170 are physically oriented opposite to each other.

FIG. 4B illustrates an example embodiment of a distal end that includes two sensors. FIG. 4B shows a cutaway view of the distal end 1001. The distal end 1001 includes two sensors 170 that are aligned along their longitudinal axes, but, in this embodiment, the sensors 170 do not include a tool channel that extends through the sensors 170. Also, the two sensors 170 are both positioned on one side of the distal end 1001. And, in this embodiment, one of the sensors 170 is wired such that its detected orientation is opposite to the other sensor 170. However, as noted above, in some embodiments the sensors 170 are physically oriented opposite to each other.

FIG. 4C illustrates an example embodiment of a distal end that includes two sensors. FIG. 4C shows a cutaway view of the distal end 1001. In this embodiment, the sensors 170 are positioned in the tool channel 150, which extends through the anchor ring 120A and the wire-guiding rings 120.

FIG. 4D illustrates an example embodiment of a distal end that includes four sensors. FIG. 4D shows a cutaway view of the distal end 1001. In this embodiment, two sensors 170 are positioned on a distal side of the anchor ring 120A and two sensors that are positioned in the tool channel 150 on a proximal side of the anchor ring 120A.

And some embodiments may include a combination of the sensors in FIGS. 2B, 3A, 3B, 3C, 3D, 4A, 4B, 4C, and 4D. For example, some embodiments may include a sensor 170 that has a tool channel 150 through its center (from FIG. 4A) and a sensor 170 from FIG. 4B.

Although some embodiments of the catheter sheath 100 fix the sensors 170 relative to each other, in some embodiments (e.g., as shown in FIG. 4D) at least some sensors 170 are positioned such that they can change positions or orientations relative to at least some of the other sensors 170. Thus, some embodiments of the navigation system 1 obtain signals 75 from the actuation-control sensors 74, calculate the relative bend angle between the sensors 170 based on the signals 75, and use this angle to calculate at least one position or orientation of at least one of the sensors 170 or to calculate a position and orientation of the distal end 1001.

The field generator 6 generates an electromagnetic field that can be detected (e.g., measured) by the two sensors 170, and the two sensors 170 then return respective signals, that are based on the detected electromagnetic field, to the navigation system 1 or the controller system 2. The navigation system 1 or the controller system 2 then determines respective positions and orientations of the sensors 170 based on the signals and determines the position and orientation of the distal end 1001 of the catheter sheath 100 based on the respective positions and orientations of the sensors 170. And, when determining the position and orientation of the distal end 1001, the navigation system 1 or the controller system 2 corrects, or compensates for, measurements errors in the positions or orientations of the sensors 170.

Figure 5:
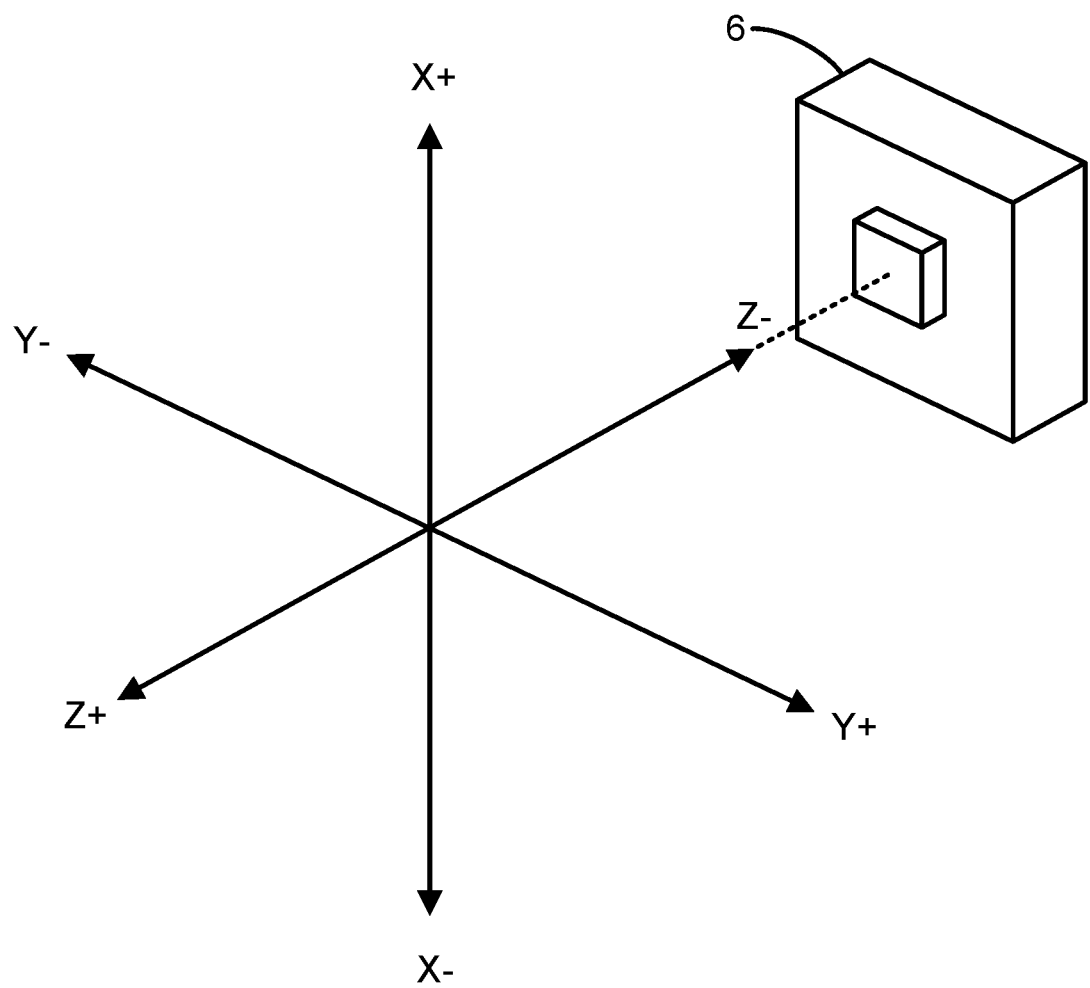
FIG. 5 illustrates an example embodiment of a field generator and a coordinate system.

The position and orientation of the distal end 1001 and the positions and orientations of the sensors 170 can be defined in a three-dimensional space. For example, FIG. 5 illustrates an example embodiment of a field generator 6 and a coordinate system. In FIG. 5, the z axis is perpendicular to the field generator's face. The y axis runs horizontal to the field generator's face, and the x axis is vertical relative to the field generator's face. The x,y position 0,0 is in the middle or center of the field generator's face.

The position of a sensor 170 can be described as an x,y,z location, and the orientation of a sensor 170 can be described as a quaternion ($Q_0$, $Q_x$, $Q_y$) or a vector, which may indicate a direction relative to the coordinates of the position. For example, Table 1 shows an example of a sensor position and orientation:

TABLE 1

| | Position | | Orientation |
|---|---|---|---|
| x | 95.07 | $Q_0$ | 0.6978 |
| y | 49.83 | $Q_x$ | −0.7117 |
| z | −127.40 | $Q_y$ | −0.0817 |

The respective signals from the two (or more) sensors 170 can allow the navigation system 1 or the controller system 2 to account for, and correct, measurement errors. A measurement error may include a position error, an orientation error, or both. For example, an embodiment of a distal end 1001 that included two sensors (both of which were NDI Aurora 5DOF sensor #610157), one of which was wired opposite to the other sensor, was placed in six different orientations while the position of the distal end remained the same. One orientation of the distal end 1001 pointed along the positive z axis, two orientations were +15 and −15 degrees from the positive z axis, one orientation pointed along the negative z axis, and two orientations were +15 and −15 degrees from the negative z axis. The orientation-measurement errors are shown in Table 2.

TABLE 2

|  | Z− | | | Z+ | | |
|---|---|---|---|---|---|---|
|  | −15° | 0° | 15° | −15° | 0° | 15° |
| Sensor 1 error (in degrees): | 2 | 2 | 0 | 27 | 46 | 5 |
| Sensor 2 error (in degrees): | 4 | 30 | 0 | 0 | 5 | 6 |

As shown by Table 2, when one sensor had a large error, the other sensor had an error that was low enough to be acceptable. Thus, using both of the sensors 170, the position and orientation of the distal end 1001 can be determined more accurately, and measurement errors can be identified or corrected.

Also, the navigation system 1 may generate an image that indicates, or is based on, the position and orientation of the distal end of the catheter sheath 100 relative to the sample (e.g., in the sample). And, based on the position and the orientation, the navigation system 1 may generate an image (e.g., a mixed-reality image, and augmented reality image) that shows the surroundings (e.g., regions of the sample, such as a lumen or cavity) of the distal of the catheter sheath 100.

Figure 6:
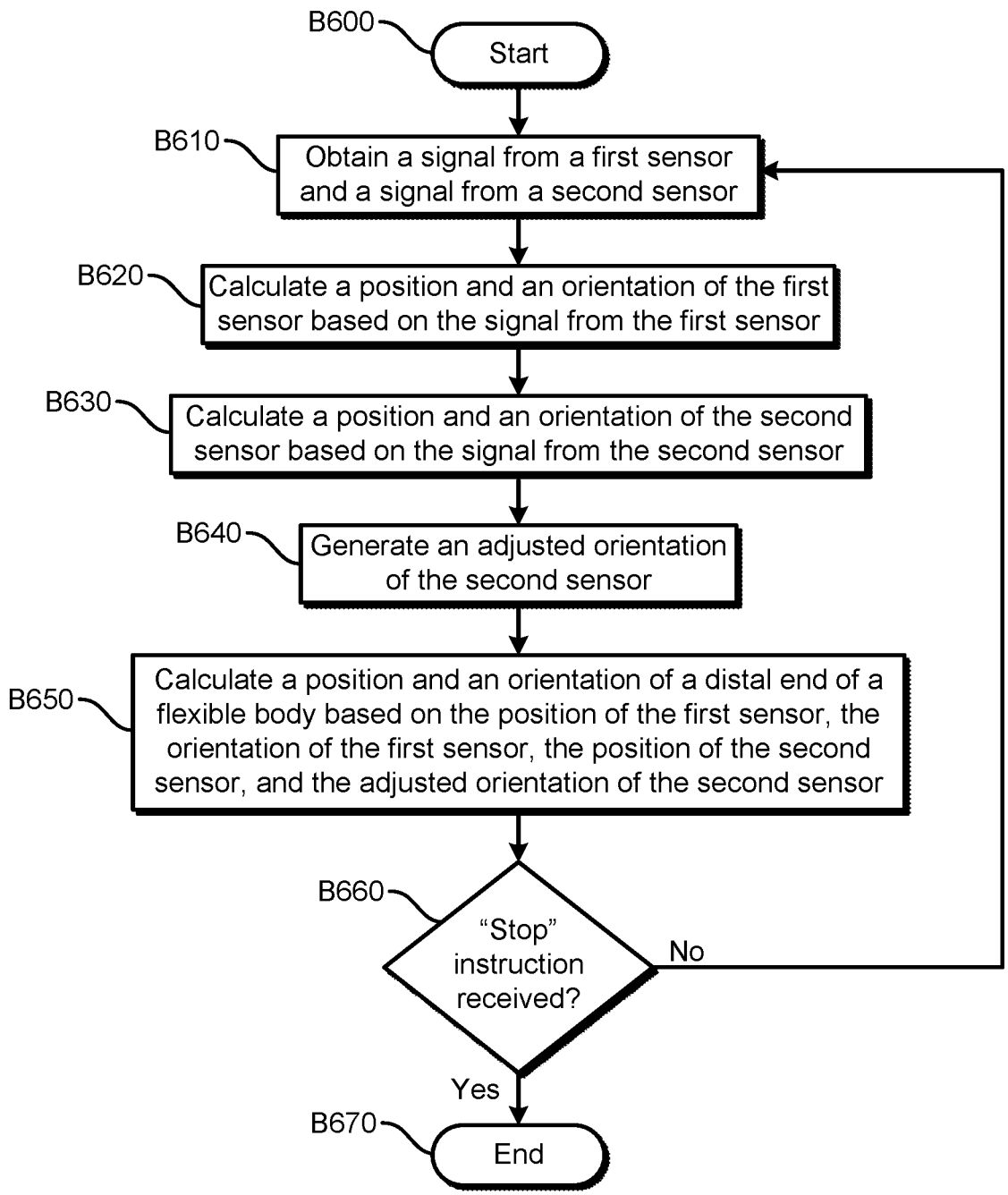
FIG. 6 illustrates an example embodiment of an operational flow for calculating a position and an orientation of a distal end of a tubular flexible body (e.g., a tubular flexible body of a bendable medical device).

FIG. 6 illustrates an example embodiment of an operational flow for calculating a position and an orientation of a distal end 1001 of a catheter sheath 100 (or other tubular flexible body). Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. And some embodiments of the operational flows may include blocks from two or more of the operational flows that are described herein. Thus, other embodiments of the operational flows that are described herein may omit blocks, add blocks, change the order of the blocks, combine blocks, or divide blocks into more blocks.

Furthermore, although the operational flows that are described herein are performed by a navigation system, some embodiments of these operational flows are performed by two or more navigation systems, by a controller system, by a navigation system working with a controller system, or by one or more other specially-configured computing devices.

In FIG. 6, the flow starts in block B600 and then moves to block B610, where a navigation system obtains a signal from a first sensor and obtains a signal from a second sensor, both of which are located at a distal end of a tubular flexible body (e.g., a catheter sheath 100). Additionally, the second sensor is wired or physically oriented such that the second sensor detects that its orientation is opposite to, or approximately opposite to, the orientation of the first sensor and to the orientation of the distal end.

The flow then moves to block B620, where the navigation system calculates a position and an orientation of the first sensor based on the signal from the first sensor. Next, in block B630, the navigation system calculates a position and an orientation of the second sensor based on the signal from the second sensor. The flow then moves to block B640, where the navigation system generates an adjusted orientation of the second sensor. For example, the navigation system may perform a 180° transformation (e.g., a 180° rotation on every one of the x, y, and z axes) on the calculated orientation of the second sensor.

The flow then proceeds to block B650, where the navigation system calculates a position and an orientation of the distal end of the tubular flexible body based on the position of the first sensor, the orientation of the first sensor, the position of the second sensor, and the adjusted orientation of the second sensor. For example, the navigation system may calculate an average of the positions of the sensors and may calculate an average of the orientation of the first sensor and of the adjusted orientation of the second sensor. Or the navigation system may select the position of one sensor and discard the other, and the navigation system may select one of the orientation of the first sensor and the adjusted orientation of the second sensor, and then discard the other. Also for example, some embodiments of block B650 include at least some of the operations that are described in FIG. 9, FIG. 10, FIG. 11, FIG. 12, and FIG. 13.

Next, the flow moves to block B660, where the navigation system determines whether a "stop" instruction has been received. If the navigation system determines that a "stop" instruction has not been received (B660=No), then the flow returns to block B610, and the navigation system continues to calculate the position and the orientation of the distal end. If the navigation system determines that a "stop" instruction has been received (B660=Yes), then the flow ends in block B670.

Also, the navigation system may generate a user interface that displays the position and the orientation of the distal end of the tubular flexible body (e.g., catheter sheath 100). For example, the navigation system may generate a user interface that displays the position and the orientation of the distal end in the form of coordinates and a vector. And the navigation system may generate an image that is based on the position and the orientation of the distal end, such as an augmented-reality or virtual-reality view of the scene that surrounds the distal end of a tubular flexible body.

Figure 7:
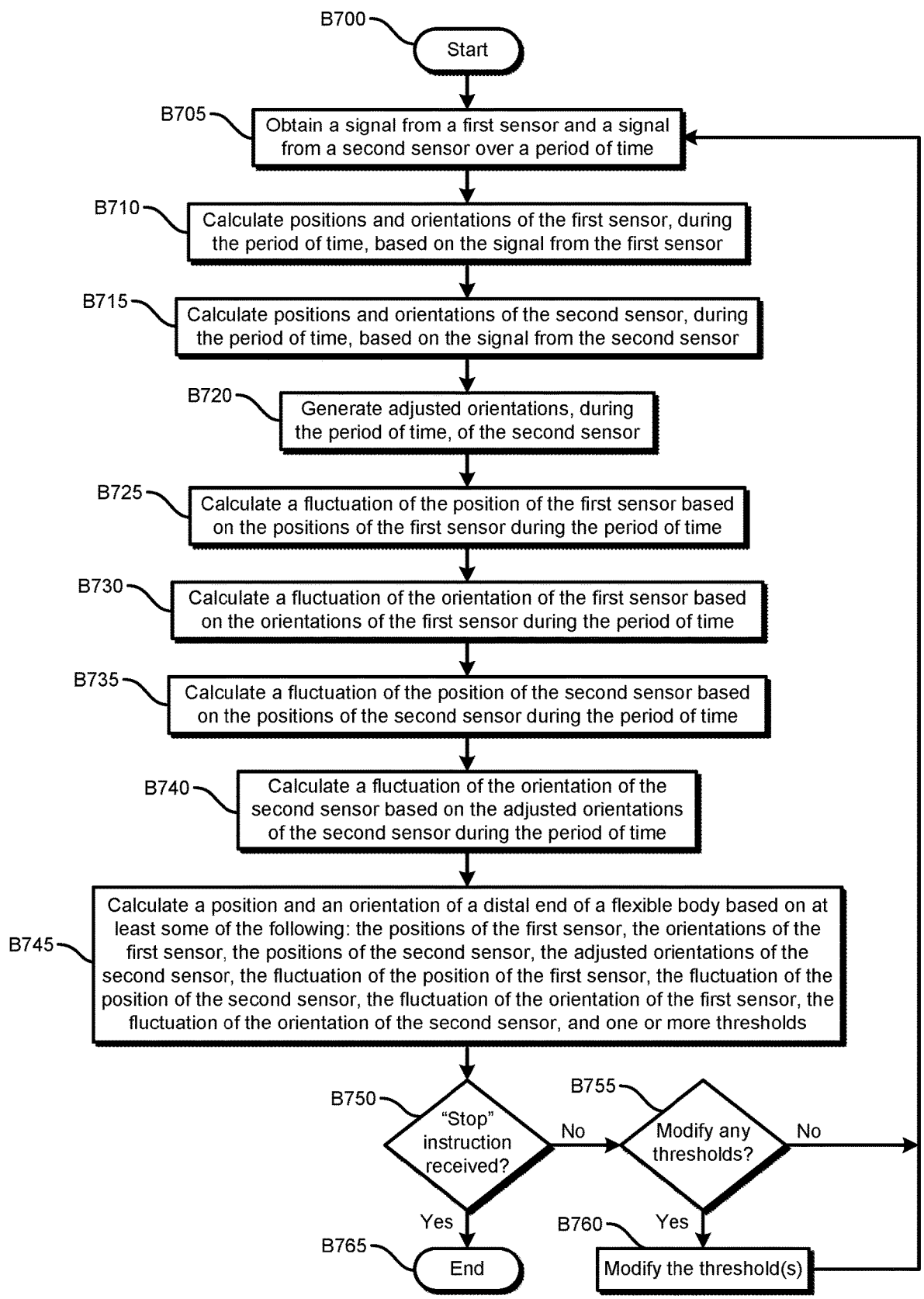
FIG. 7 illustrates an example embodiment of an operational flow for calculating a position and an orientation of a distal end of a tubular flexible body.

FIG. 7 illustrates an example embodiment of an operational flow for calculating a position and an orientation of a distal end of a tubular flexible body (e.g., catheter sheath). The flow starts in block B700 and then moves to block B705, where a navigation system obtains a signal from a first sensor and a signal from a second sensor over a period of time. The signals may vary over the period of time. At least some of the variations may be caused by sensor drift, which may be a change in the signal (which indicates one or both of a change of position or of orientation) due to the amount of time the sensor has been active.

Next, in block B710, the navigation system calculates positions and orientations of the first sensor, during the period of time, based on the signal from the first sensor. The variations in the signal may indicate different positions or orientations. Thus, during the period of time, the navigation system may calculate multiple positions and multiple orientations of the first sensor.

Then, in block B715, the navigation system calculates positions and orientations of the second sensor, during the period of time, based on the signal from the second sensor. Thus, during the period of time, the navigation system may calculate multiple positions and multiple orientations for the second sensor. Also, in block B720, the navigation system generates adjusted (e.g., transformed) orientations, during the period of time, of the second sensor.

Figure 8A:
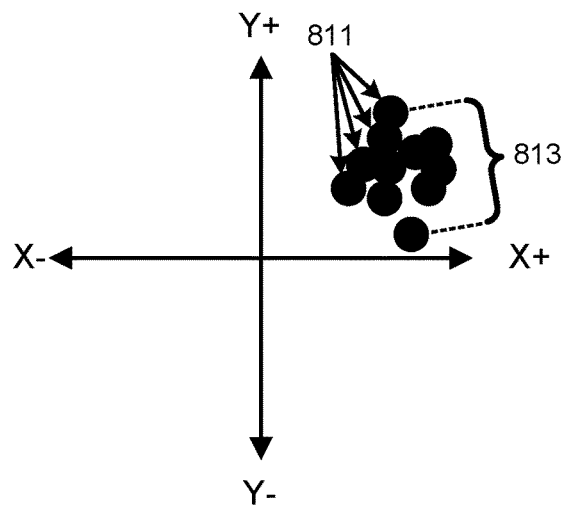
FIG. 8A illustrates an example embodiment of a fluctuation of a position.
Figure 8B:
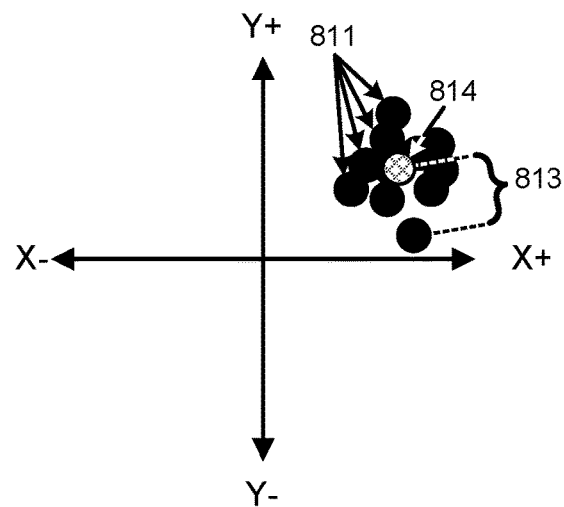
FIG. 8B illustrates an example embodiment of a fluctuation of a position.

The flow then moves to block B725, where the navigation system calculates a fluctuation (which may indicate a difference between two values or indicate a range of values) of the position of the first sensor based on the positions of the first sensor during the period of time. The fluctuation of the position (position fluctuation) may indicate the range of the variations (e.g., shifting back and forth) of the positions of a sensor (e.g., the first sensor) that are indicated by the signal from the sensor. For example, FIG. 8A illustrates an example embodiment of a fluctuation of a position. FIG. 8A shows the positions 811 of a sensor that are indicated by a signal over a period of time. In this embodiment, the position fluctuation 813 is the distance between the two positions 811 that are farthest from each other (the maximum distance of all the distances between pairs of positions during the period of time). However, in some embodiments the position fluctuation 813 is the mean, the median, or the variance of the distances between the positions 811. And, in some embodiments, such as the example embodiment in FIG. 8B, the position fluctuation 813 is the distance between (1) the average position 814 of the positions 811 and (2) the position 811 that is farthest from the average position 814. Also, although FIGS. 8A-B show the positions 811 and the position fluctuations 813 in two-dimensional space, the positions 811 may be defined in three-dimensional space, and the position fluctuations 813 may be calculated in three-dimensional space.

For example, Table 3 illustrates the position fluctuations of two sensors, which were orientated in different orientations but which stayed in the same position, over a period of approximately 2 seconds.

TABLE 3

| | Z− | | | Z+ | | |
| | | | Orientation | | | |
| | −15° | 0° | 15° | −15° | 0° | 15° |
| Sensor 1 Position fluctuation in mm | 0.001 | 0.0007 | 0.001 | 0.01 | 0.05 | 0.01 |
| Sensor 2 Position fluctuation in mm | 0.01 | 0.04 | 0.006 | 0.001 | 0.002 | 0.002 |

Figure 8C:
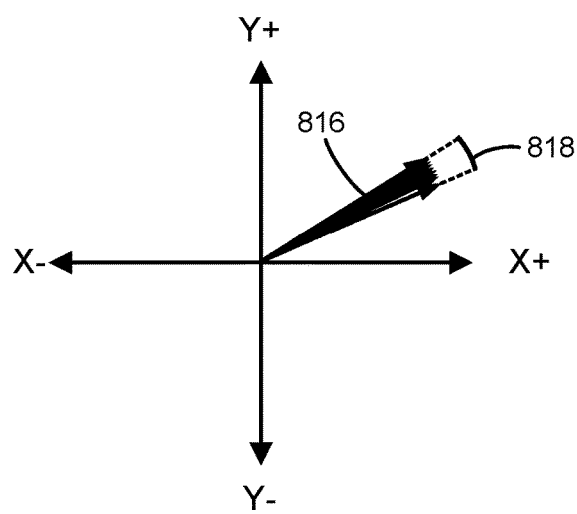
FIG. 8C illustrates an example embodiment of a fluctuation of an orientation.
Figure 8D:
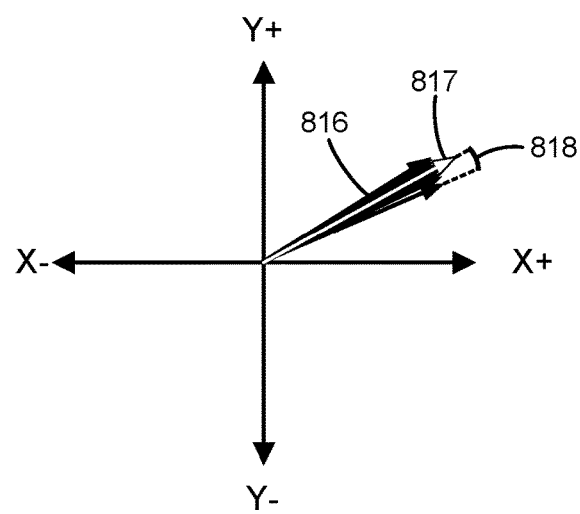
FIG. 8D illustrates an example embodiment of a fluctuation of an orientation.

Next, in block B730, the navigation system calculates a fluctuation of the orientation of the first sensor based on the orientations of the first sensor during the period of time. The orientation fluctuation may indicate a range of the variations (e.g., shifting back and forth) of the orientations of a sensor (e.g., the first sensor) that are indicated by the signal from the sensor. For example, FIG. 8C illustrates an example embodiment of a fluctuation of an orientation. FIG. 8C shows the orientations 816 of a sensor that are indicated by a signal over a period of time. In this embodiment, the orientation fluctuation 818 is the angle between the two angles 816 that are farthest from each other (the maximum angle of all the angles between pairs of orientations during the period of time). However, in some embodiments the orientation fluctuation 818 is the mean, the median, or the variance of the angles between the orientations 816. And, in some embodiments, such as the example embodiment in FIG. 8D, the orientation fluctuation 818 is the angle between (1) the average orientation 817 of the orientations 816 and (2) the orientation 816 that is farthest from the average orientation 817. Also, although FIGS. 8C-D show the orientations 816 and the orientation fluctuations 818 in two-dimensional space, the orientations 816 may be defined in three-dimensional space, and the orientation fluctuations 818 may be calculated in three-dimensional space.

The flow then proceeds to block B735, where the navigation system calculates a fluctuation of the position of the second sensor based on the positions of the second sensor during the period of time. Then, in block B740, the navigation system calculates a fluctuation of the orientation of the second sensor based on the adjusted orientations of the second sensor during the period of time.

The flow then moves to block B745, where the navigation system calculates a position and an orientation of a distal end of a tubular flexible body (e.g., a catheter sheath) based on at least some of the following: the positions of the first sensor, the orientations of the first sensor, the positions of the second sensor, the adjusted orientations of the second sensor, the fluctuation of the position of the first sensor, the fluctuation of the position of the second sensor, the fluctuation of the orientation of the first sensor, the fluctuation of the orientation of the second sensor, and one or more thresholds (e.g., a position-fluctuation threshold, an orientation-fluctuation threshold). Also, for example, some embodiments of block B745 include at least some of the operations in FIG. 9, FIG. 10, FIG. 11, FIG. 12, and FIG. 13.

Furthermore, at least some of the operations in blocks B705-6745 can be performed concurrently.

Next, in block B750, the navigation system determines whether it has received a "stop" instruction. If the navigation system determines that is has received a "stop" instruction (B750=Yes), then the flow ends in block B765.

If the navigation system determines that is has not received a "stop" instruction (B750=No), then the flow proceeds to block B755. In block B755, the navigation system determines whether to modify any thresholds. For example, the navigation system may determine to modify one or more thresholds if one or both of the sensors have moved closer to the field generator since the one or more thresholds were generated, if one or both of the sensors have moved farther from the field generator since the one or more thresholds were generated, if the respective orientations of one or more of the sensors have changed since the one or more thresholds were generated, or if the strengths of the respective signals from the one or more sensors have changed since the one or more thresholds were generated.

If the navigation system determines not to modify any threshold (B755=No), then the flow returns to block B705, and a new period of time starts. If the navigation system determines to modify one or more thresholds (B755=Yes), then the flow advances to block B760. In block B760, the navigation system modifies the one or more thresholds that it determined to modify in block B755. For example, the navigation system may increase a threshold as the sensors move farther from the field generator, and the navigation system may decrease a threshold as the sensors move closer to the field generator. Then the flow returns to block B705, and a new period of time starts.

Also, thresholds may be continually or continuously updated by the navigation system. And, in some embodiments, thresholds are continually or continuously updated to incorporate the sensors' distances from the field generator as variables because sensor-measurement errors may increase as the sensors' distances from the field generator increase.

Figure 9:
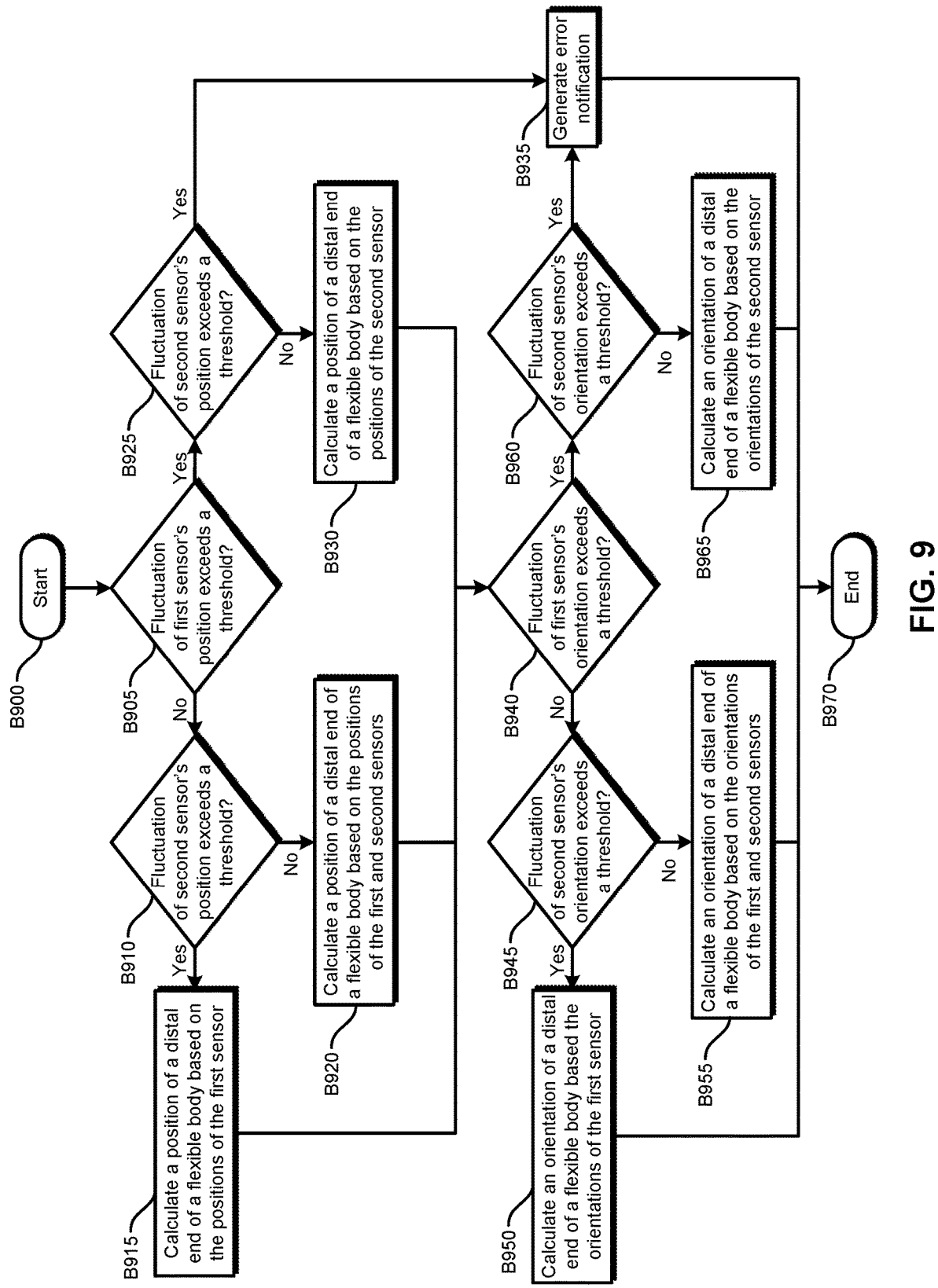
FIG. 9 illustrates an example embodiment of an operational flow for calculating a position and an orientation of a distal end of a tubular flexible body.

FIG. 9 illustrates an example embodiment of an operational flow for calculating a position and an orientation of a distal end of a tubular flexible body (e.g., a catheter sheath). The flow begins in block B900 and then moves to block B905, where a navigation system determines if the fluctuation of a first sensor's position exceeds a threshold.

A threshold may be defined as a difference (delta) between the fluctuations (position fluctuations, orientation fluctuations) of the sensors (e.g., a difference that is greater than 0.005 mm), and the threshold may be defined as a difference (delta) between a reference fluctuation and a currently considered fluctuation. Also, the reference fluctuation may be the lowest of the fluctuations. Thus, in some embodiments, the lowest position fluctuation is used as the reference fluctuation for determining whether a position fluctuation exceeds a threshold (a position-fluctuation threshold) in blocks B905, B910, and B925 (i.e., the navigation system determines whether the difference between a currently considered position fluctuation and the lowest position fluctuation exceeds a threshold). For example, referring to Table 3, in the Z-orientation of −15°, because the position fluctuation of sensor 1 is lower than the position fluctuation of sensor 2, the navigation system may use the position fluctuation of sensor 1 (0.001 mm) as a reference for the threshold. And, when sensor 1 is the currently considered position fluctuation, because the difference between the position fluctuation of sensor 1 (0.001 mm) and the reference fluctuation (which is the position fluctuation of sensor 1) is less than the threshold (because the difference is zero), the navigation system would determine that the position fluctuation of sensor 1 does not exceed the threshold. But, using 0.005 as the threshold, the difference between the reference fluctuation (0.001 mm) and the position fluctuation of sensor 2 (0.01 mm) is greater than 0.005, so the navigation system would determine (e.g., in block B910) that the position fluctuation of sensor 2 exceeds the threshold.

Additionally, the threshold may be a set numerical value.

If the navigation system determines that the fluctuation of the first sensor's position does not exceed the threshold (B905=No), then the flow moves to block B910. If the navigation system determines that the fluctuation of the first sensor's position does exceed the threshold (B905=Yes), then the flow moves to block B925.

In block B910, the navigation system determines whether the fluctuation of the second sensor's position exceeds a threshold (which may be the same as the threshold in block B905 or a different threshold). If the navigation system determines that the fluctuation of the second sensor's position does exceed the threshold (B910=Yes), then the flow moves to block B915, where the navigation system calculates a position of a distal end of a tubular flexible body based on the positions of the first sensor. For example, the navigation system may calculate, as the position of the distal end, a median or an average of the positions of the first sensor. From block B915, the flow moves to block B940.

If the navigation system determines that the fluctuation of the second sensor's position does not exceed the threshold (B910=No), then the flow moves to block B920, where the navigation system calculates a position of the distal end of the tubular flexible body based on the positions of the first and second sensors. For example, the navigation system may calculate, as the position of the distal end, a median or an average of the positions of the first and second sensors. And, from block B920, the flow moves to block B940.

If the flow moves from block B905 to block B925, then, in block B925, the navigation system determines whether the fluctuation of the second sensor's position exceeds a threshold (which may be the same as the threshold in block B905, the same as the threshold in block B910, or a different threshold). If the navigation system determines that the fluctuation of the second sensor's position does not exceed the threshold (B925=No), then the flow moves to block B930. In block B930, the navigation system calculates a position of the distal end of the tubular flexible body based on the positions of the second sensor. For example, the navigation system may calculate, as the position of the distal end, a median or an average of the positions of the second sensor. From block B930, the flow moves to block B940.

If the navigation system determines that the fluctuation of the second sensor's position does exceed the threshold (B925=Yes), then the flow moves to block B935. In block B935, the navigation system generates an error notification, and then the flow ends in block B970. Also, in block B935, the position of the sensor can be calculated based on the positions of the sensor that has the lowest position fluctuation.

In block B940, the navigation system determines whether the fluctuation of the first sensor's orientation exceeds a threshold (an orientation-fluctuation threshold). In some embodiments, the lowest of the orientation fluctuations of the sensors is used as the reference for determining whether an orientation fluctuation exceeds a threshold in blocks B940, B945, and B960. And some embodiments use a set numerical value as the threshold.

If the navigation system determines that the fluctuation of the first sensor's orientation does not exceed the threshold (B940=No), then the flow moves to block B945. If the navigation system determines that the fluctuation of the first sensor's orientation does exceed the threshold (B940=Yes), then the flow moves to block B960.

In block B945, the navigation system determines whether the fluctuation of the second sensor's orientation exceeds a threshold (which may be the same as the threshold in block B940 or a different threshold). If the navigation system determines that the fluctuation of the second sensor's orientation does exceed the threshold (B945=Yes), then the flow moves to block B950, where the navigation system calculates an orientation of a distal end of a tubular flexible body based on the orientations of the first sensor. For example, the navigation system may calculate, as the orientation of the distal end, a median or an average of the orientations of the first sensor. From block B950, the flow moves to block B970.

If the navigation system determines that the fluctuation of the second sensor's orientation does not exceed the threshold (B945=No), then the flow moves to block B955, where the navigation system calculates an orientation of a distal end of a tubular flexible body based on the orientations of the first and second sensors. For example, the navigation system may calculate, as the orientation of the distal end, a median or an average of the orientations of the first and second sensors. Also, the orientations of one of the first and second sensors are adjusted orientations. And, from block B955, the flow moves to block B970.

If the flow moves from block B940 to block B960, then, in block B960, the navigation system determines whether the fluctuation of the second sensor's orientation exceeds a threshold (which may be the same as the threshold in block B940, the same as the threshold in block B945, or a different threshold). If the navigation system determines that the fluctuation of the second sensor's orientation does not exceed the threshold (B960=No), then the flow moves to block B965. In block B965, the navigation system calculates an orientation of a distal end of a tubular flexible body based on the orientations (e.g., adjusted orientations) of the second sensor. For example, the navigation system may calculate, as the orientation of the distal end, a median or an average of the adjusted orientations of the second sensor. From block B965, the flow moves to block B970.

If the navigation system determines that the fluctuation of the second sensor's orientation does exceed the threshold (B960=Yes), then the flow moves to block B935, where the navigation system generates an error notification. Also, in block B935, the orientation of the sensor can be calculated based on the sensor that has the lowest orientation fluctuation.

Finally, the flow ends in block B970.

Thus, in various embodiments, a threshold can be defined by a delta of individual points, by a delta of sensor orientation, or by a delta of sensor position. And the advantages of relative thresholds can include reducing sensor drift because the sensors may have similar drift in their respective measurements.

Figure 10:
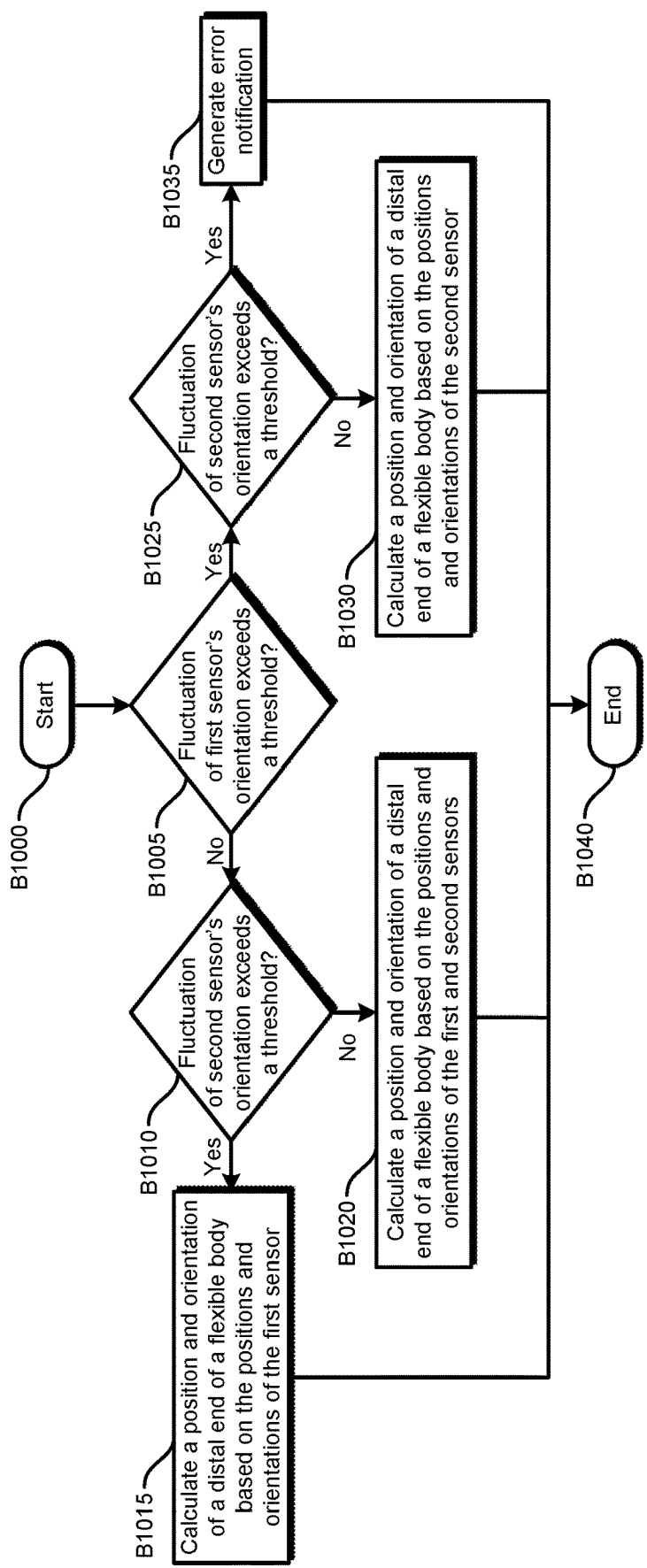
FIG. 10 illustrates an example embodiment of an operational flow for calculating a position and an orientation of a distal end of a tubular flexible body.

FIG. 10 illustrates an example embodiment of an operational flow for calculating a position and an orientation of a distal end of a tubular flexible body (e.g., a catheter sheath 100). The flow begins in block B1000 and then moves to block B1005, where a navigation system determines whether the fluctuation of a first sensor's orientation exceeds a threshold. If the navigation system determines that the fluctuation of the first sensor's orientation does not exceed the threshold (B1005=No), then the flow moves to block B1010. If the navigation system determines that the fluctuation of the first sensor's orientation does exceed the threshold (B1005=Yes), then the flow moves to block B1025.

In block B1010, the navigation system determines whether the fluctuation of the second sensor's orientation exceeds a threshold (which may be the same as the threshold in block B1005 or a different threshold). If the navigation system determines that the fluctuation of the second sensor's orientation does exceed the threshold (B1010=Yes), then the flow moves to block B1015, where the navigation system calculates a position and an orientation of a distal end of a tubular flexible body based on the positions and the orientations of the first sensor. For example, the navigation system may calculate, as the position of the distal end, a median or an average position of the first sensor, and the navigation system may calculate, as the orientation of the distal end, a median or an average orientation of the first sensor. From block B1015, the flow moves to block B1040.

If the navigation system determines that the fluctuation of the second sensor's orientation does not exceed the threshold (B1010=No), then the flow moves to block B1020, where the navigation system calculates a position and an orientation of the distal end of the tubular flexible body based on the positions and the orientations of the first and second sensors. For example, the navigation system may calculate, as the position of the distal end, a median or an average of the positions of the first and second sensors, and the navigation system may calculate, as the orientation of the distal end, a median or an average of the orientations of the first and second sensors (and the orientations of either the first sensor or the second sensor may be adjusted orientations). And, from block B1020, the flow moves to block B1040.

If the flow moves from block B1005 to block B1025, then, in block B1025, the navigation system determines whether the fluctuation of the second sensor's orientation exceeds a threshold (which may be the same as the threshold in block B1005, the same as the threshold in block B1010, or a different threshold). If the navigation system determines that the fluctuation of the second sensor's orientation does not exceed the threshold (B1025=No), then the flow moves to block B1030. In block B1030, the navigation system calculates a position and an orientation of the distal end of the tubular flexible body based on the positions and the orientations of the second sensor. For example, the navigation system may calculate, as the position of the distal end, a median or an average position of the second sensor, and the navigation system may calculate, as the orientation of the distal end, a median or an average orientation (e.g., a median or an average adjusted orientation) of the second sensor. From block B1030, the flow moves to block B1040.

If the navigation system determines that the fluctuation of the second sensor's orientation does exceed the threshold (B1025=Yes), then the flow moves to block B1035, where the navigation system generates an error notification.

Finally, the flow ends in block B1040.

Figure 11:
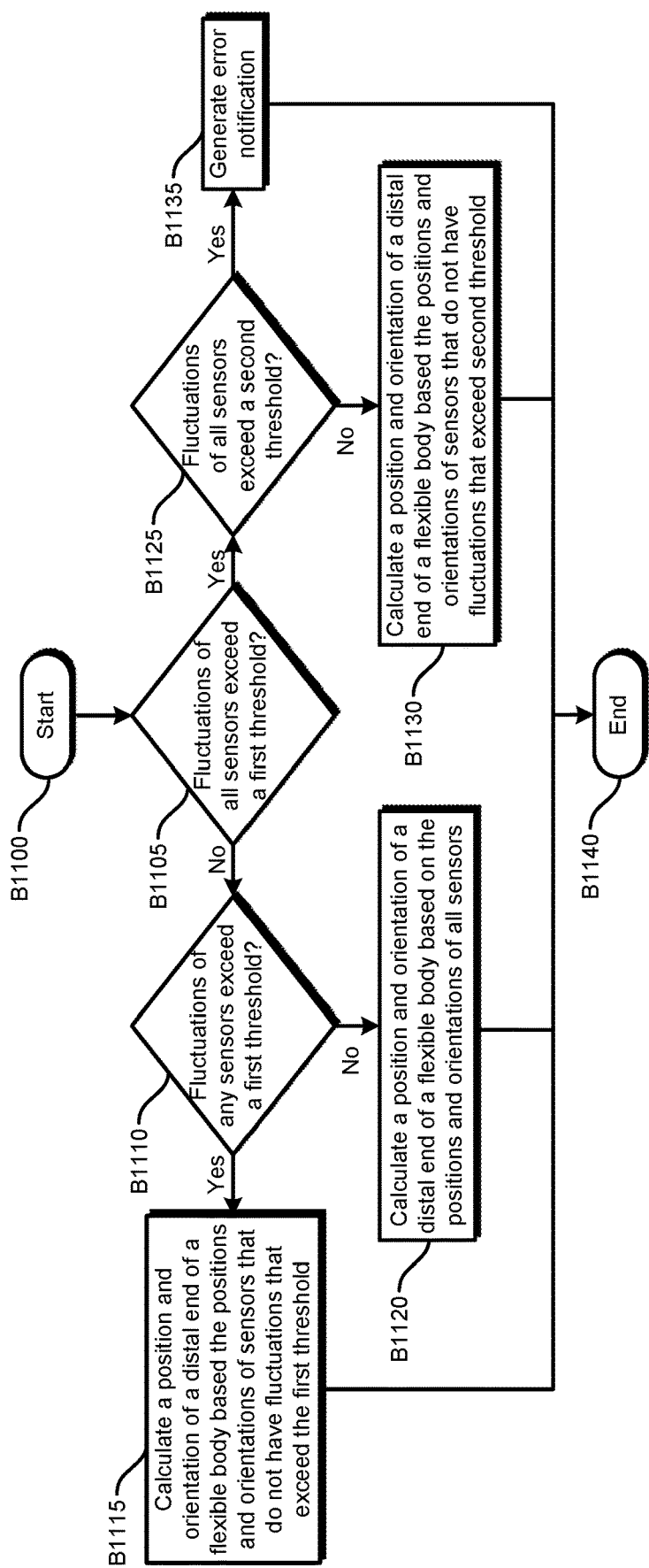
FIG. 11 illustrates an example embodiment of an operational flow for calculating a position and an orientation of a distal end of a tubular flexible body.

FIG. 11 illustrates an example embodiment of an operational flow for calculating a position and an orientation of a distal end of a tubular flexible body. The flow begins in block B1100 and then moves to block B1105, where a navigation system determines whether all of the respective position fluctuations, orientation fluctuations, or both position and orientation fluctuations of all sensors exceed a first threshold (or, when different thresholds are used for position and orientation, first thresholds). If the navigation system determines that at least some of the fluctuations do not exceed the first threshold (or first thresholds) (B1105=No), then the flow moves to block B1110. If the navigation system determines that all of the fluctuations do exceed the first threshold (or first thresholds) (B1105=Yes), then the flow moves to block B1125.

In block B1110, the navigation system determines whether the respective fluctuations of any of the sensors exceed the first threshold (or first thresholds). If the navigation system determines that at least some of the fluctuations of the sensors exceed the first threshold (or first thresholds) (B1110=Yes), then the flow moves to block B1115, where the navigation system calculates a position and an orientation of a distal end of a tubular flexible body based on the respective positions and orientations of the sensors that do not have fluctuations that exceed the first threshold (or first thresholds). And, from block B1115, the flow moves to block B1140.

If the navigation system determines that none the respective fluctuations of the sensors exceed the first threshold (or first thresholds) (B1110=No), then the flow moves to block B1120, where the navigation system calculates a position and an orientation of the distal end of the tubular flexible body based on the respective positions and orientations of all sensors. Then, from block B1120, the flow moves to block B1140.

If the navigation system determines that all the fluctuations of all sensors exceed the first threshold (or first thresholds) (B1105=Yes), then the flow moves to block B1125, where the navigation system determines whether all the respective fluctuations of all sensors exceed a second threshold (or, when different thresholds are used for position and orientation, second thresholds). If the navigation system determines that all the respective fluctuations of all sensors do not exceed the second threshold (or second thresholds) (i.e., at least some of the respective fluctuations of one or more sensors do not exceed the second threshold), then the flow proceeds to block B1130. In block B1130, the navigation system calculates a position and an orientation of the distal end of the tubular flexible body based on the respective positions and orientations of the sensors that do not have fluctuations that exceed the second threshold (or second thresholds), and then the flow moves to block B1140.

If the navigation system determines that all the respective fluctuations of all sensors do exceed the second threshold (or second thresholds) (B1125=Yes), then the flow proceeds to block B1135, where the navigation system generates an error notification. The flow then moves to block B1140.

Finally, the flow ends in block B1140.

Figure 12:
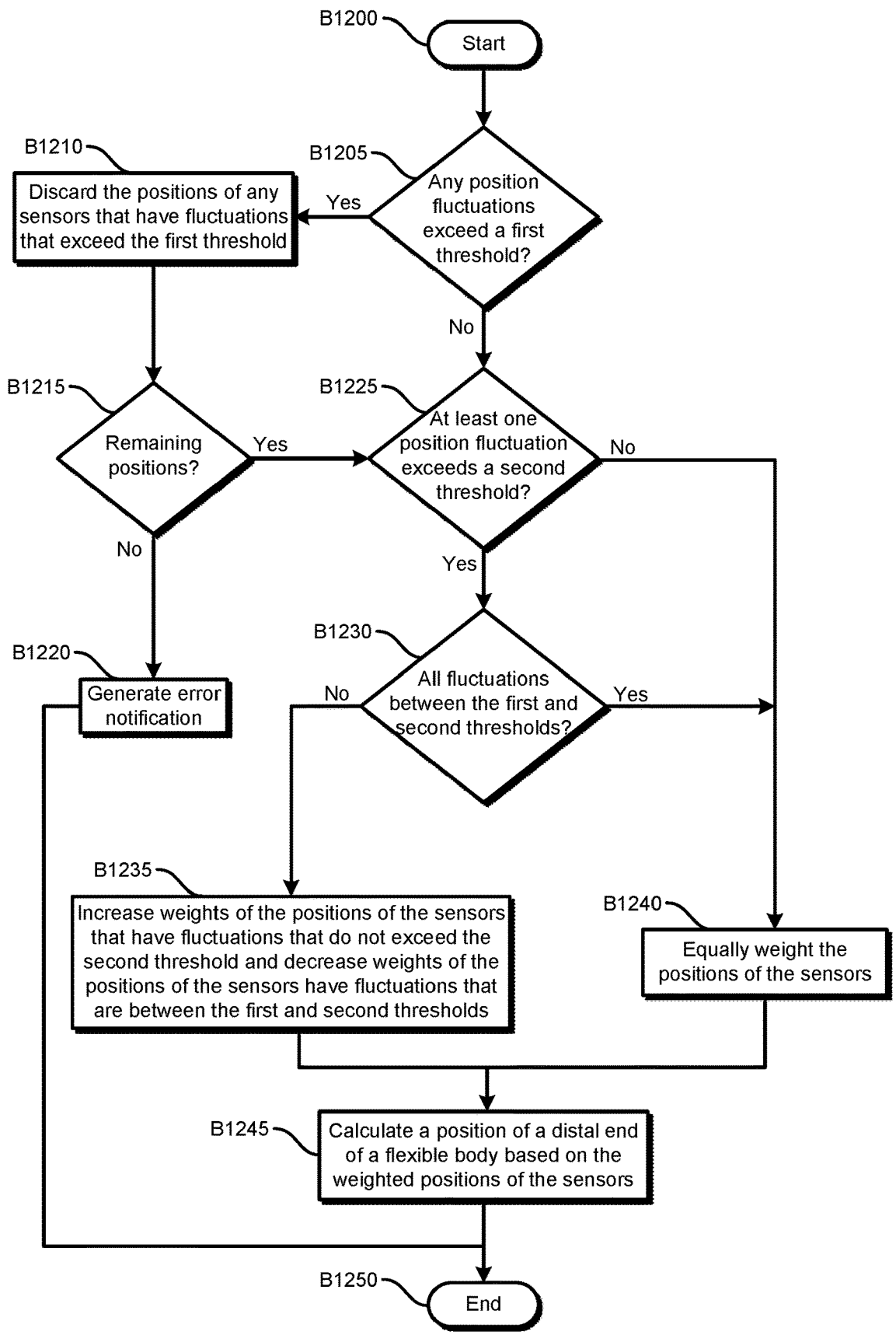
FIG. 12 illustrates an example embodiment of an operational flow for calculating a position of a distal end of a tubular flexible body.

FIG. 12 illustrates an example embodiment of an operational flow for calculating a position of a distal end of a tubular flexible body (e.g., a catheter sheath 100). The flow starts in block B1200 and moves to block B1205, where a navigation system determines whether the respective fluctuations of the positions of any sensors (which include two or more sensors) exceed a first threshold. If the navigation system determines that at least one of the respective fluctuations of the positions of the sensors exceeds the first threshold (B1205=Yes), then the flow moves to block B1210. If the navigation system determines that none of the respective fluctuations of the positions of the sensors exceed the first threshold (B1205=No), then the flow moves to block B1225.

In block B1210, the navigation system discards the positions of any sensors that have position fluctuations that exceed the first threshold. Then, in block B1215, the navigation system determines whether there are any remaining positions (i.e., whether any sensors have positions fluctuations that do not exceed the first threshold). If the navigation system determines that there are not any remaining positions (B1215=No), then the flow moves to block B1220, where the navigation system generates an error notification, and then the flow ends in block B1250. If the navigation system determines that there are remaining positions (B1215=Yes), then the flow proceeds to block B1225.

In block B1225, the navigation system determines whether at least one (undiscarded) position fluctuation exceeds a second threshold that is smaller than the first threshold. If the navigation system determines that no position fluctuation exceeds the second threshold (i.e., all of the position fluctuations are lower than the second threshold, which is lower than the first threshold) (B1225=No), then the flow moves to block B1240. If the navigation system determines that at least one position fluctuation exceeds the second threshold (B1225=Yes), then the flow moves to block B1230.

In block B1230, the navigation system determines whether all of the (undiscarded) position fluctuations are between the first and second thresholds. If the navigation system determines that all of the position fluctuations are between the first and second thresholds (B1230=Yes), then the flow moves to block B1240. If the navigation system determines that not all of the position fluctuations are between the first and second thresholds (e.g., at least one position fluctuation is below the second threshold and at least one position fluctuation is between the first and second thresholds) (B1230=No), then the flow moves to block B1235.

In block B1235, the navigation system increases respective weights of the (undiscarded) positions of the sensors that have fluctuations that do not exceed the second threshold (which is lower than the first threshold) and decreases respective weights of the (undiscarded) positions of the sensors that have fluctuations that are between the first and second thresholds. For example, in embodiments that have two sensors, the default weighting may be 50% and 50%. However, as the position fluctuation of one sensor exceeds the second threshold and approaches the first threshold, the weighting of that sensor could decrease, until it eventually reaches 0% when the fluctuation reaches the first threshold. And the weighting of the sensor that does not exceed the second threshold could increase by the amount by which the weight of the other sensor (which has a fluctuation that exceeds the second threshold) decreases, which would equal 100% when the weight of the other sensor equals 0%. Also, the weighting may be based on a variance of one or more fluctuations. The flow then moves to block B1245.

In block B1240, the navigation system equally weights the positions of the (undiscarded) sensors. The flow then advances to block B1245.

In block B1245, the navigation system calculates a position of a distal end of a tubular flexible body based on the weighted positions of the sensors. Also, the navigation system may weight the orientations of the sensors according to the same weights that were used for the respective positions of the sensors (i.e., a sensor's orientations may be weighted with the same weight as the sensor's positions) and calculate an orientation of the distal end of the tubular flexible body based on the weighted orientations.

Finally, the flow ends in block B1250.

Figure 13:
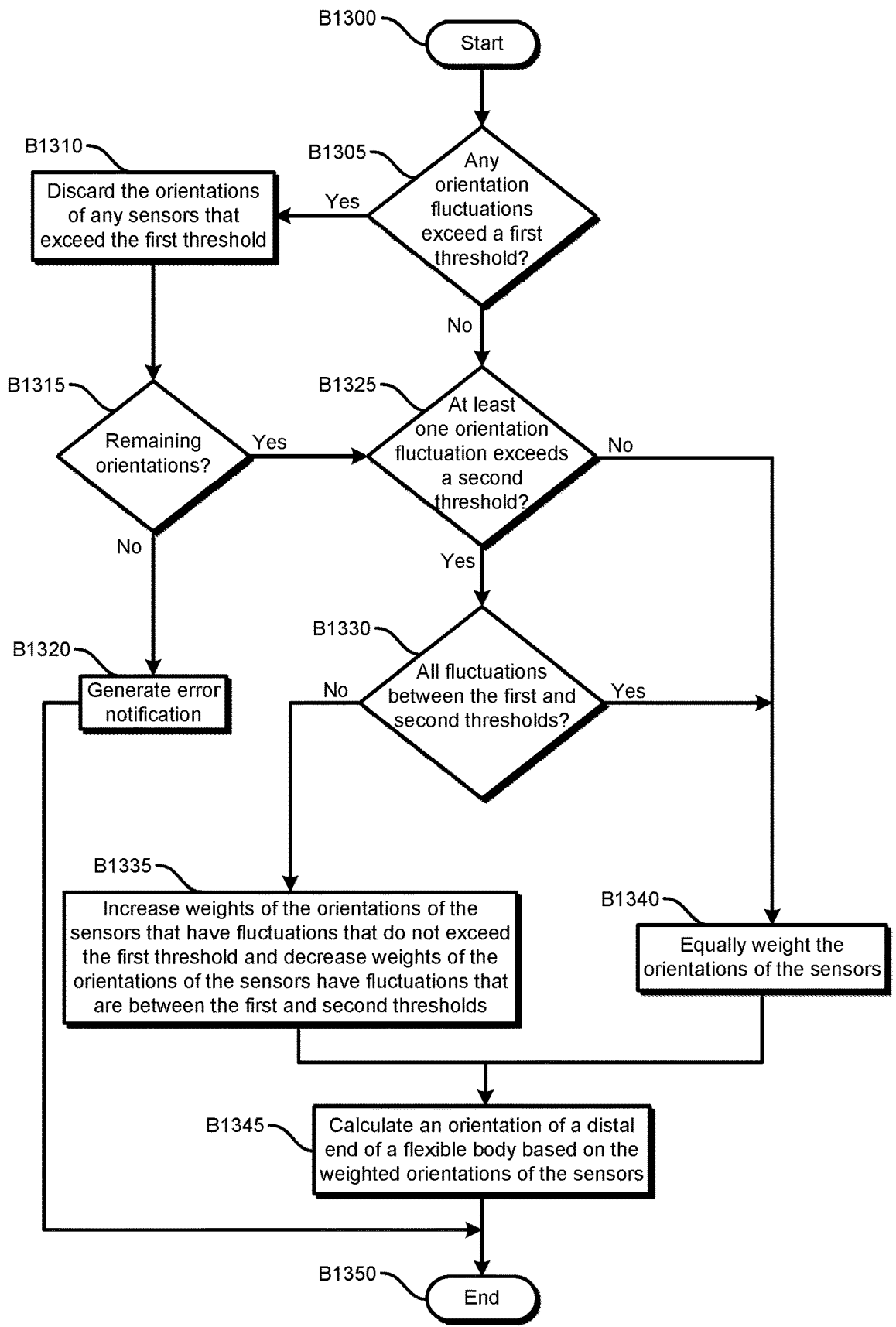
FIG. 13 illustrates an example embodiment of an operational flow for calculating an orientation of a distal end of a tubular flexible body.

FIG. 13 illustrates an example embodiment of an operational flow for calculating an orientation of a distal end of a tubular flexible body (e.g., a catheter sheath 100). The flow starts in block B1300 and moves to block B1305, where a navigation system determines whether any of the respective fluctuations of the orientations (which may be adjusted orientations) of any sensors (which include two or more sensors) exceed a first threshold. If the navigation system determines that at least one of the respective fluctuations of the orientations of the sensors exceeds the first threshold (B1305=Yes), then the flow moves to block B1310. If the navigation system determines that none of the respective fluctuations of the orientations of the sensors exceed the first threshold (B1305=No), then the flow moves to block B1325.

In block B1310, the navigation system discards the orientations of any sensors that have orientation fluctuations that exceed the first threshold. Then, in block B1315, the navigation system determines whether there are any remaining orientations (i.e., whether any sensors have orientation fluctuations that do not exceed the first threshold). If the navigation system determines that there are not any remaining orientations (B1315=No), then the flow moves to block B1320, where the navigation system generates an error notification, and then the flow ends in block B1350. If the navigation system determines that there are remaining orientations (B1315=Yes), then the flow proceeds to block B1325.

In block B1325, the navigation system determines whether at least one (undiscarded) orientation fluctuation exceeds a second threshold that is smaller than the first threshold. If the navigation system determines that no orientation fluctuation exceeds the second threshold (i.e., all of the orientation fluctuations are lower than the second threshold, which is lower than the first threshold) (B1325=No), then the flow moves to block B1340. If the navigation system determines that at least one orientation fluctuation exceeds the second threshold (B1325=Yes), then the flow moves to block B1330.

In block B1330, the navigation system determines whether all of the (undiscarded) orientation fluctuations are between the first and second thresholds. If the navigation system determines that all of the orientation fluctuations are between the first and second thresholds (B1330=Yes), then the flow moves to block B1340. If the navigation system determines that not all of the orientation fluctuations are between the first and second thresholds (e.g., at least one orientation fluctuation is below the second threshold and at least one orientation fluctuation is between the first and second thresholds) (B1330=No), then the flow moves to block B1335.

In block B1335, the navigation system increases respective weights of the (undiscarded) orientations of the sensors that have fluctuations that do not exceed the second threshold (which is lower than the first threshold) and decreases respective weights of the (undiscarded) orientations of the sensors that have fluctuations that are between the first and second thresholds. For example, in embodiments that have two sensors, the default weighting may be 50% and 50%. However, as the orientation fluctuation of one sensor exceeds the second threshold and approaches the first threshold, the weighting of that sensor could decrease, until it eventually reaches 0% when the fluctuation reaches the first threshold. And the weighting of the sensor that does not exceed the second threshold could increase by the amount by which the weight of the other sensor (which has a fluctuation that exceeds the second threshold) decreases, which would equal 100% when the weight of the other sensor equals 0%. The flow then moves to block B1345.

In block B1340, the navigation system equally weights the orientations of the (undiscarded) sensors. The flow then advances to block B1345.

In block B1345, the navigation system calculates an orientation of a distal end of a tubular flexible body based on the weighted orientations of the sensors. Also, the navigation system may weight the positions of the sensors according to the same weights that were used for the respective orientations of the sensors (i.e., a sensor's position may be weighted with the same weight as the sensor's orientation) and calculate a position of the distal end of the tubular flexible body based on the weighted positions.

Finally, the flow ends in block B1350.

Figure 14:
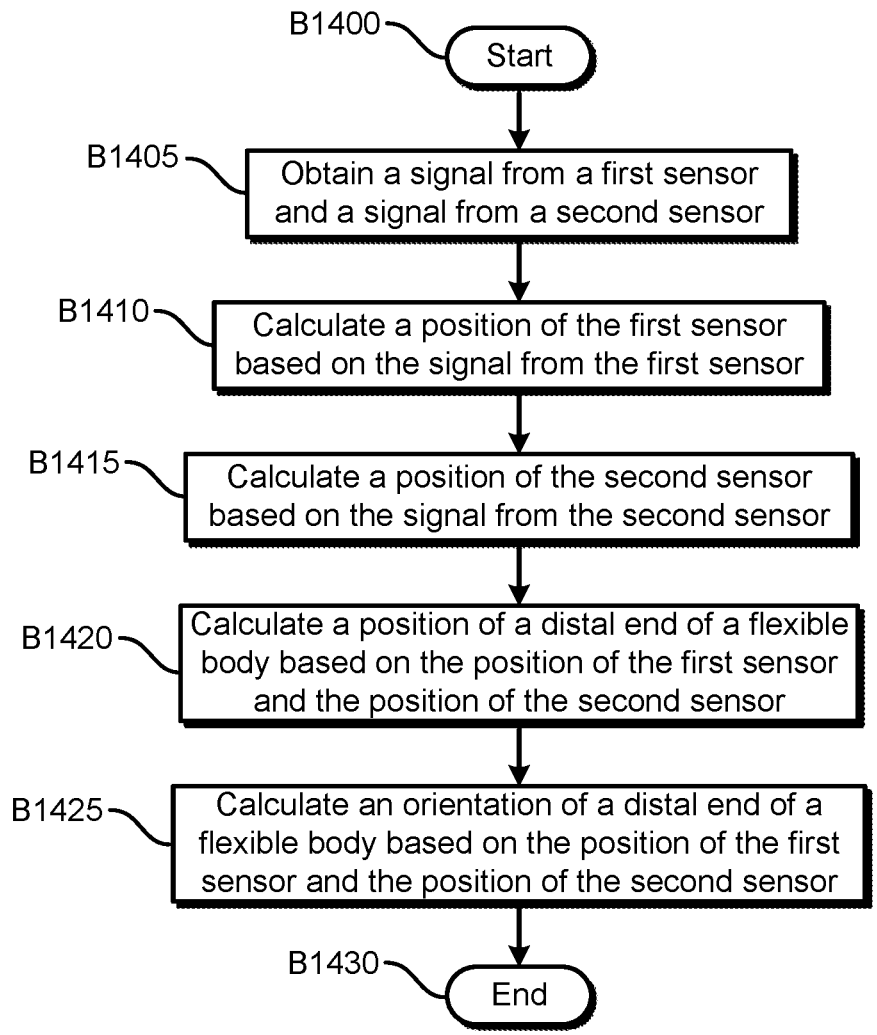
FIG. 14 illustrates an example embodiment of an operational flow for calculating a position and an orientation of a distal end of a tubular flexible body.
Figure 15:
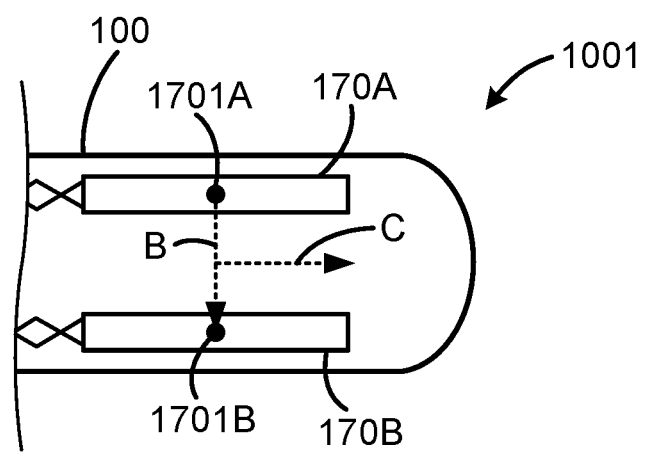
FIG. 15 illustrates an example embodiment of a vector between two sensor positions.

FIG. 14 illustrates an example embodiment of an operational flow for calculating a position and an orientation of a distal end of a tubular flexible body (e.g., a catheter sheath 100). The flow starts in block B1400 and then moves to block B1405, where a navigation system obtains a signal from a first sensor and a signal from a second sensor. Next, in block B1410, the navigation system calculates a position of the first sensor based on the signal from the first sensor. The position of the first sensor may identify the position of a datum of the first sensor. Then, in block B1415, the navigation system calculates a position of the second sensor based on the signal from the second sensor. The position of the second sensor may identify the position of a datum of the second sensor The flow then moves to block B1420, where the navigation system calculates a position of a distal end of a tubular flexible body based on the position of the first sensor and the position of the second sensor. Then, in block B1425, the navigation system calculates an orientation of a distal end of a tubular flexible body based on the position of the first sensor and on the position of the second sensor. For example, a vector between the positions of the two sensors (e.g., the positions of the datums of the two sensors) may be calculated. Also, because the sensors are fixed in the distal end of the tubular flexible body, the vector can be used to calculate the orientation of the tubular flexible body, for example by transforming the vector by 90°. Thus, even if the orientations of the sensors cannot be calculated based on the signals from the sensors, the navigation system can still calculate the orientation of the distal end. For example, FIG. 15 illustrates an example embodiment of a vector, vector B, between the positions of two sensor 170. In this example, vector B is a vector between the datum 1701A of a first sensor 170A and the datum 1701B of the second sensor 170B. By rotating vector B by 90°, vector C, which indicates the orientation of the distal end 1001, can be obtained. Some embodiments derive the orientation of the distal end from vector C, and some embodiments use vector C to identify which of the sensors 170 has detected an accurate orientation.

Finally, the flow ends in block B1430.

Figure 16:
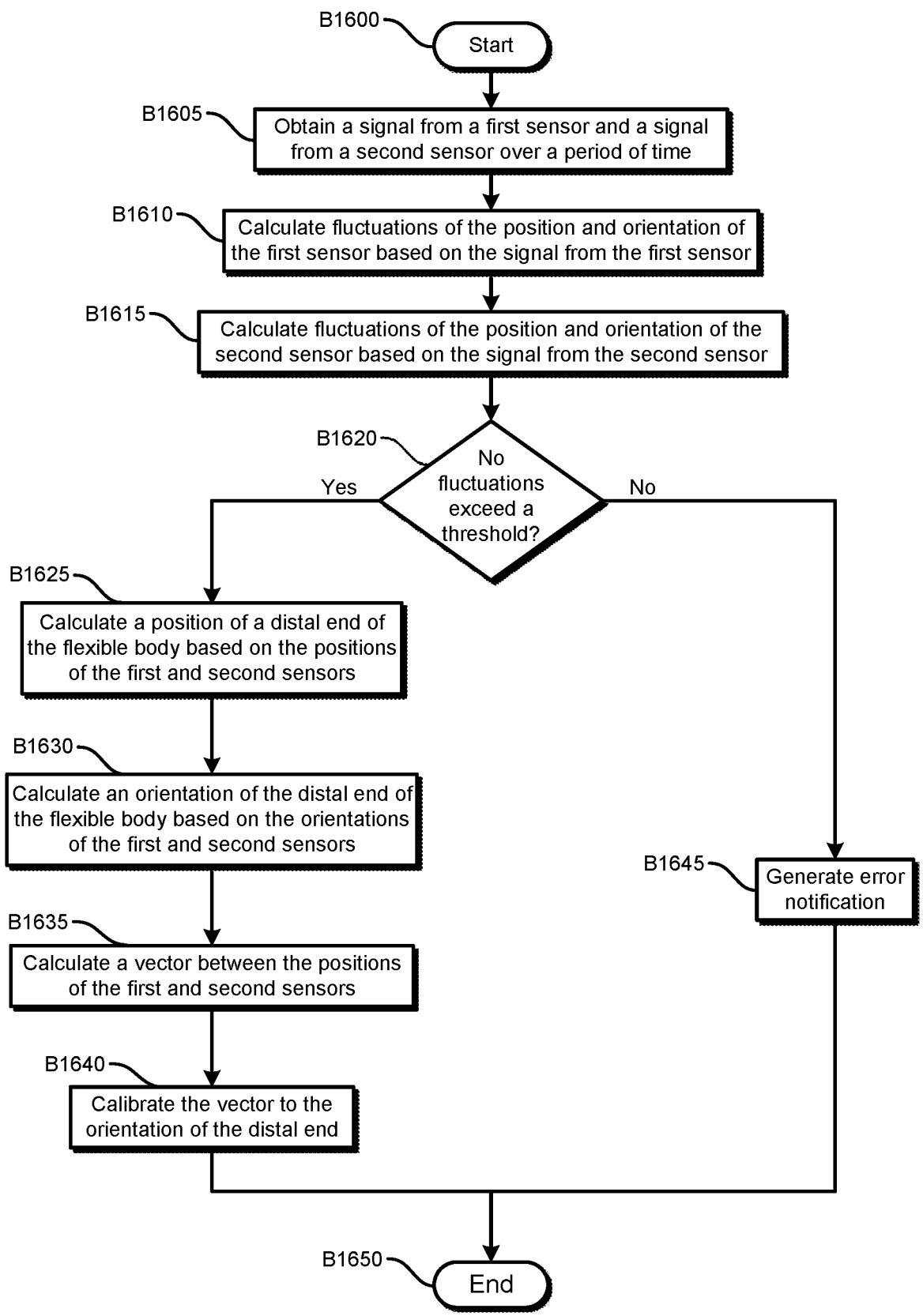
FIG. 16 illustrates an example embodiment of an operational flow for calibrating a vector to an orientation of a tubular flexible body.

FIG. 16 illustrates an example embodiment of an operational flow for calibrating a vector to an orientation of a tubular flexible body (e.g., a catheter sheath 100). The flow starts in block B1600 and then moves to block B1605, where, over a period of time, a navigation system obtains a signal from a first sensor and obtains a signal from a second sensor. Next, in block B1610, the navigation system calculates fluctuations of the position and orientation of the first sensor based on the signal from the first sensor. And, in block B1615, the navigation system calculates fluctuations of the position and orientation of the second sensor based on the signal from the second sensor.

The flow then moves to block B1620, where the navigation system determines whether any of the fluctuations exceed a threshold. If none of the fluctuations exceed the threshold (B1620=Yes), then the flow moves to block B1625. If one or more of the fluctuations exceed the threshold (B1620=No), then the flow moves to block B1645, where the navigation system generates an error notification that indicates that the calibration could not be completed, and then the flow ends in block B1650.

In block B1625, the navigation system calculates a position of a distal end of a tubular flexible body based on the positions of the first and second sensors. Then, in block B1630, the navigation system calculates an orientation of the distal end based on the orientations of the first and second sensors. Next, in block B1635, the navigation system calculates a vector between the positions of the first and second sensors. The flow then moves to block B1640, where the navigation system calibrates the vector to the orientation of the distal end. For example, the navigation system may calculate a transformation that translates the vector to the orientation.

Then the flow ends in block B1650.

Also, the calibration of the vector to the orientation may be done by another computing device (e.g., at the time of manufacture), and the calibration data (including the transformation) and data that indicate the relative positions of the sensors may be stored in a computer-readable storage media in the tubular flexible body. Such embodiments could eliminate the need for a user or system to perform the calibration operations.

Figure 17:
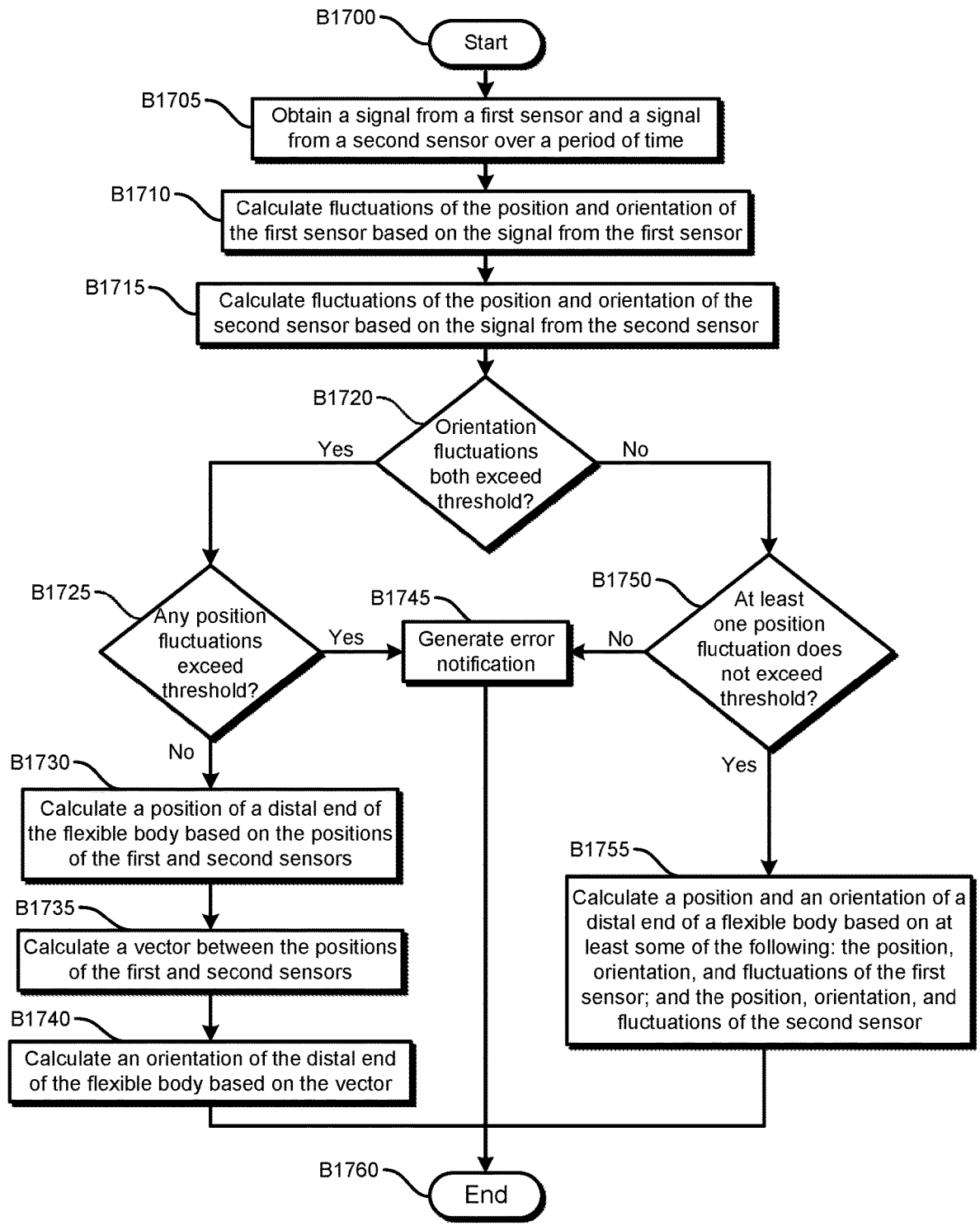
FIG. 17 illustrates an example embodiment of an operational flow for calculating a position and an orientation of a distal end of a tubular flexible body.

FIG. 17 illustrates an example embodiment of an operational flow for calculating a position and an orientation of a distal end of a tubular flexible body (e.g., a catheter sheath 100). The flow begins in block B1700 and moves to block B1705, where a navigation system obtains, over a period of time, a signal from a first sensor and a signal from a second sensor. Then, in block B1710, the navigation system calculates fluctuations of the position and orientation of the first sensor based on the signal from the first sensor. And, in block B1715, the navigation system calculates fluctuations of the position and orientation of the second sensor based on the signal from the second sensor.

The flow then advances to block B1720, where the navigation system determines whether the orientation fluctuations of both the first and second sensors exceed a threshold. If the navigation system determines that the orientation fluctuations of both the first and second sensors exceed a threshold (B1720=Yes), then the flow moves to block B1725. If the navigation system determines that the respective orientation fluctuation of at least one of the first and second sensors does not exceed the threshold (B1720=No), then the flow proceeds to block B1750.

In block B1725, the navigation system determines whether any of the position fluctuations of the first and second sensors exceed a threshold (which may be different than the threshold in block B1720). If the navigation system determines that none of the position fluctuations of the first and second sensors exceed the threshold (i.e., the fluctuations of the orientations of both sensors exceed the applicable threshold and none of the fluctuations of the positions of the sensors exceed the applicable threshold) (B1725=No), then the flow moves to block B1730. If the navigation system determines that one or more of the position fluctuations of the first and second sensors exceed the threshold (B1725=Yes), then the flow moves to block B1745.

In block B1730, the navigation system calculates a position of a distal end of a tubular flexible body based on the positions of the first and second sensors. Then, in block B1735, the navigation system calculates a vector between the positions of the first and second sensors. And, in block B1740, the navigation system calculates an orientation of the distal end based on the vector and, in some embodiments, on calibration data (which may include a transformation and data that indicate the relative positions of the sensors). The flow then ends in block B1760.

If the flow moves from block B1720 to block B1750, in block B1750 the navigation system determines whether the position fluctuation of at least one sensor does not exceed a threshold (which may be different than the threshold in block B1720 and may be different than the threshold in block B1725). If the navigation system determines that the position fluctuation of at least one sensor does not exceed the threshold (i.e., the fluctuation of the position of at least one sensor does not exceed the applicable threshold and the fluctuation of the orientation of at least one sensor does not exceed the applicable threshold) (B1750=Yes), then the flow moves to block B1755. If the navigation system determines that the position fluctuations of both sensors do exceed the threshold (B1750=No), then the flow moves to block B1745.

In block B1755, the navigation system calculates a position and an orientation of the distal end of the tubular flexible body based on at least some of the following: the position of the first sensor if the fluctuation of the position does not exceed the threshold (in block B1750), the orientation of the first sensor if the fluctuation of the orientation does not exceed the threshold (in block B1720), the fluctuation of the position of the first sensor if the fluctuation of the position does not exceed the threshold (in block B1750), the fluctuation of the orientation of the first sensor if the fluctuation of the orientation does not exceed the threshold (in block B1720), the position of the second sensor if the fluctuation of the position does not exceed the threshold (in block B1750), the orientation of the second sensor if the fluctuation of the orientation does not exceed the threshold (in block B1720), the fluctuation of the position of the second sensor if the fluctuation of the position does not exceed the threshold (in block B1750), and the fluctuation of the orientation of the second sensor if the fluctuation of the orientation does not exceed the threshold (in block B1720). Then the flow ends in block B1760.

And, if the flow proceeds to block B1745, then, in block B1745, the navigation system generates an error notification. Then the flow ends in block B1760.

Figure 18:
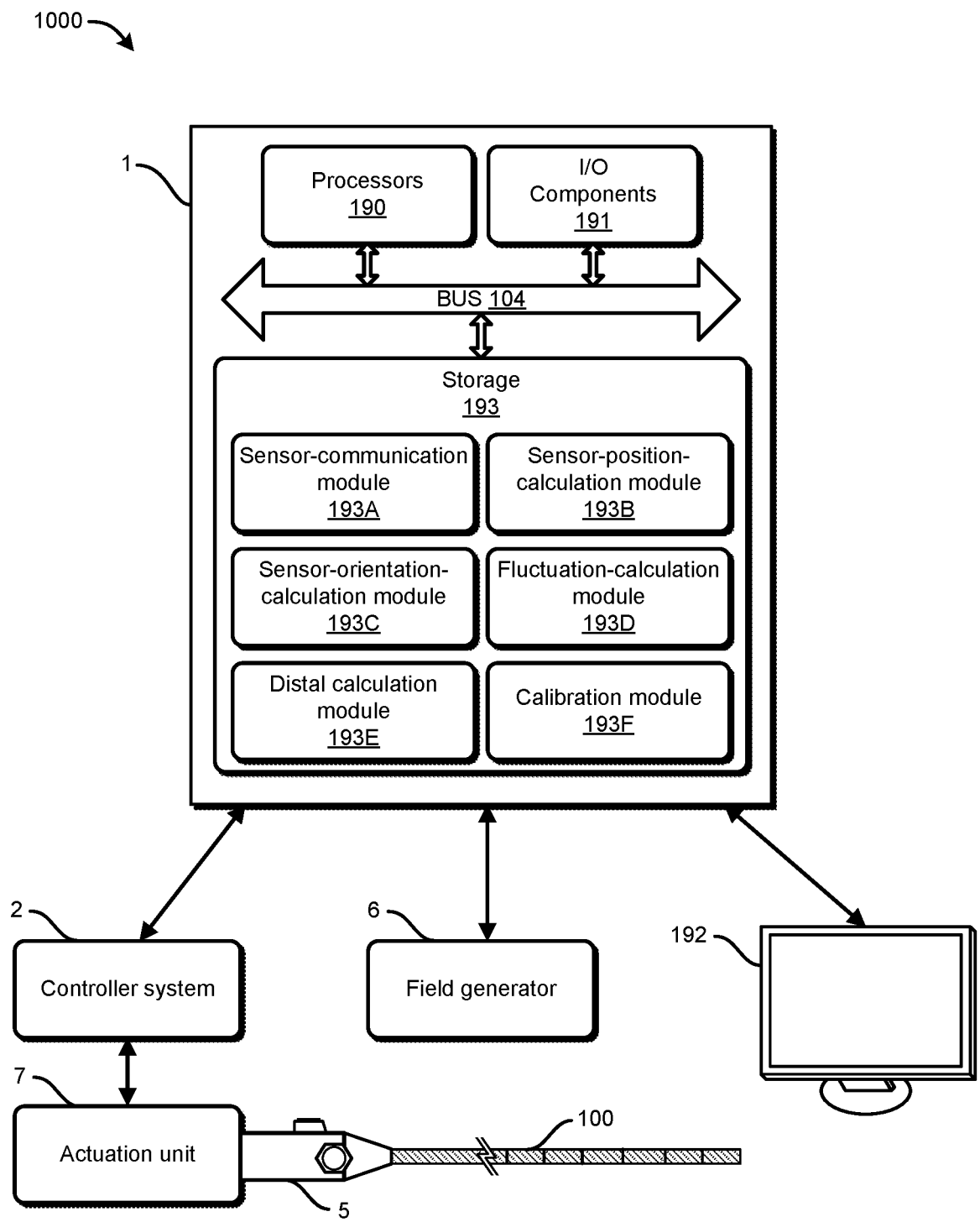
FIG. 18 illustrates an example embodiment of a medical system.

FIG. 18 illustrates an example embodiment of a medical system 1000. The medical system 1000 includes a navigation system 1, which is a specially-configured computing device; a controller system 2; a connector assembly 5; an actuation unit 7; a tubular flexible body (which is catheter sheath 100 in this embodiment); a field generator 6; and a display device 192.

The navigation system 1 includes one or more processors 190, one or more I/O components 191, and storage 193. Also, the hardware components of the navigation system 1 communicate via one or more buses 104 or other electrical connections. Examples of buses 104 include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 190 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 191 include communication components (e.g., a GPU, a network-interface controller) that communicate with the display device 192, the controller system 2, the field generator 6, a network (not shown), and other input or output devices (not illustrated), which may include a keyboard, a mouse, a printing device, a touch screen, a light pen, an optical-storage device, a scanner, a microphone, a drive, a joystick, and a control pad.

The storage 193 includes one or more computer-readable storage media. As used herein, a computer-readable storage medium refers to a computer-readable medium that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage 193, which may include both ROM and RAM, can store computer-readable data or computer-executable instructions.

The navigation system 1 additionally includes a sensor-communication module 193A, a sensor-position-calculation module 193B, a sensor-orientation-calculation module 193C, a fluctuation-calculation module 193D, a distal-calculation module 193E, and a calibration module 193F. A module includes logic, computer-readable data, or computer-executable instructions. In the embodiment shown in FIG. 18, the modules are implemented in software (e.g., Assembly, C, C++, C#, Java, BASIC, Perl, Visual Basic). However, in some embodiments, the modules are implemented in hardware (e.g., customized circuitry) or, alternatively, a combination of software and hardware. When the modules are implemented, at least in part, in software, then the software can be stored in the storage 193. Also, in some embodiments, the navigation system 1 includes additional or fewer modules, the modules are combined into fewer modules, or the modules are divided into more modules.

The sensor-communication module 193A includes instructions that cause the navigation system 1 to receive signals from sensors. For example, some embodiments of the sensor-communication module 193A include instructions that cause the navigation system 1 to perform at least some of the operations that are described in block B610 in FIG. 6, in block B705 in FIG. 7, in block B1405 in FIG. 14, in block B1605 in FIG. 16, and in block B1705 in FIG. 17.

The sensor-position-calculation module 193B includes instructions that cause the navigation system 1 to calculate the respective positions of sensors based on signals from the sensors. For example, some embodiments of the sensor-position-calculation module 193B include instructions that cause the navigation system 1 to perform at least some of the operations that are described in blocks B620-6630 in FIG. 6, in blocks B710-6715 in FIG. 7, in blocks B1410-61415 in FIG. 14, in blocks B1610-B1615 in FIG. 16, and in blocks B1710-61715 in FIG. 17.

The sensor-orientation-calculation module 193C includes instructions that cause the navigation system 1 to calculate the respective orientations of sensors, which may include adjusted orientations. For example, some embodiments of the sensor-orientation-calculation module 193C include instructions that cause the navigation system 1 to perform at least some of the operations that are described in blocks B620-B640 in FIG. 6, in blocks B710-6720 in FIG. 7, in blocks B1610-61615 in FIG. 16, and in blocks B1710-61715 in FIG. 17.

The fluctuation-calculation module 193D includes instructions that cause the navigation system 1 to calculate fluctuations in the positions or fluctuations in the orientations of sensors. For example, some embodiments of the fluctuation-calculation module 193D include instructions that cause the navigation system 1 to perform at least some of the operations that are described in blocks B725-6740 in FIG. 7, in blocks B1610-61615 in FIG. 16, and in blocks B1710-61715 in FIG. 17.

The distal-calculation module 193E includes instructions that cause the navigation system 1 to calculate the position or the orientation of a distal end of the catheter sheath 100 (or another a tubular flexible body) and, in some embodiments, to modify one or more thresholds. For example, some embodiments of the distal-calculation module 193E include instructions that cause the navigation system 1 to perform at least some of the operations that are described in blocks B650-6660 in FIG. 6, in blocks B745-6760 in FIG. 7, in blocks B900-6970 in FIG. 9, in blocks B1000-B1040 in FIG. 10, in blocks B1100-61140 in FIG. 11, in blocks B1200-61250 in FIG. 12, in blocks B1300-61350 in FIG. 13, in blocks B1420-61425 in FIG. 14, in blocks B1620-61630 and B1645 in FIG. 16, and in blocks B1720-61755 in FIG. 17.

The calibration module 193F includes instructions that cause the navigation system 1 to calibrate the vector between the positions of sensors (e.g., the positions of the sensors' datums) to an orientation of a distal end of a catheter sheath 100 (or another tubular flexible body) and to generate calibration data (e.g., transformations). For example, some embodiments of the calibration module 193F include instructions that cause the navigation system 1 to perform at least some of the operations that are described in blocks B1635-61640 in FIG. 16.

The scope of the claims is not limited to the above-described embodiments and includes various modifications and equivalent arrangements.

The invention claimed is:

1. A device comprising:
a tubular flexible body that includes a channel through a longitudinal axis;
a first sensor that is located in a distal end of the tubular flexible body;
a second sensor that is located in the distal end of the tubular flexible body; and
wiring that connects to the first sensor and the second sensor and that extends to a proximal end of the tubular flexible body,
wherein a sensed orientation of the first sensor is oriented opposite to a sensed orientation of the second sensor
wherein a distance between the first sensor and the second sensor is fixed, and
wherein an orientation of the first sensor is fixed relative to an orientation of the second sensor.

2. The device of claim 1, wherein the distance between the first sensor and the second sensor is less than or equal to 5 millimeters and is greater than or equal to 2 millimeters.

3. The device of claim 1, further comprising:
a third sensor.

4. The device of claim 1, wherein
the first sensor is a five-degree-of-freedom sensor or is a six-degree-of-freedom sensor, and
the second sensor is a five-degree-of-freedom sensor or is a six-degree-of-freedom sensor.

5. A device comprising:
a tubular flexible body that includes a channel through a longitudinal axis;
a first sensor that is located in a distal end of the tubular flexible body;
a second sensor that is located in the distal end of the tubular flexible body; and
wiring that connects to the first sensor and the second sensor and that extends to a proximal end of the tubular flexible body,
wherein a sensed orientation of the first sensor is oriented opposite to a sensed orientation of the second sensor,
wherein the first sensor and the second sensor are a same model or type of sensor, and
wherein the second sensor is wired with a polarity that is opposite to a polarity of the first sensor.

6. The device of claim 5, wherein a distance between the first sensor and the second sensor is fixed, and wherein an orientation of the first sensor is fixed relative to an orientation of the second sensor.

7. The device of claim 6, wherein the distance between the first sensor and the second sensor is less than or equal to 5 millimeters and is greater than or equal to 2 millimeters.

8. The device of claim 5, further comprising:
a third sensor.

9. The device of claim 5, wherein
the first sensor is a five-degree-of-freedom sensor or is a six-degree-of-freedom sensor, and
the second sensor is a five-degree-of-freedom sensor or is a six-degree-of-freedom sensor.

10. A device comprising:
a tubular flexible body that includes a channel through a longitudinal axis;
a first sensor that is located in a distal end of the tubular flexible body;
a second sensor that is located in the distal end of the tubular flexible body; and wiring that connects to the first sensor and the second sensor and that extends to a proximal end of the tubular flexible body, wherein a sensed orientation of the first sensor is oriented opposite to a sensed orientation of the second sensor, wherein the first sensor is identical to the second sensor, and wherein the second sensor is oriented opposite to an orientation of the first sensor.

11. The device of claim 10, wherein a distance between the first sensor and the second sensor is fixed, and wherein an orientation of the first sensor is fixed relative to an orientation of the second sensor.

12. The device of claim 11, wherein the distance between the first sensor and the second sensor is less than or equal to 5 millimeters and is greater than or equal to 2 millimeters.

13. The device of claim 10, further comprising:
a third sensor.

14. The device of claim 10, wherein
the first sensor is a five-degree-of-freedom sensor or is a six-degree-of-freedom sensor, and
the second sensor is a five-degree-of-freedom sensor or is a six-degree-of-freedom sensor.

15. A medical system comprising:
a tubular flexible body that includes a channel through a longitudinal axis;
a first sensor that is located in a distal end of the tubular flexible body;
a second sensor that is located in the distal end of the tubular flexible body;
wiring that connects to the first sensor and the second sensor and that extends to a proximal end of the tubular flexible body;
one or more computer-readable storage media; and
one or more processors that are in communication with the one or more computer-readable storage media and that cooperate with the one or more computer-readable storage media to perform operations that comprise:
receiving a first signal from the first sensor, wherein the first signal indicates a position and an orientation of the first sensor,
receiving a second signal from the second sensor, wherein the second signal indicates a position and an orientation of the second sensor,
adjusting the orientation of the second sensor to an orientation that is opposite to the orientation of the second sensor, thereby generating an adjusted orientation of the second sensor, and
calculating a position and an orientation of the distal end of the tubular flexible body based on the position and the orientation of the first sensor and on the position and the adjusted orientation of the second sensor.

16. The medical system of claim 15, wherein calculating the position and the orientation of the distal end of the tubular flexible body includes:
detecting a fluctuation of the position and a fluctuation of the orientation of the first sensor over a period of time, and detecting a fluctuation of the position and a fluctuation of the adjusted orientation of the second sensor over the period of time.

17. The medical system of claim 16, wherein calculating the position and the orientation of the distal end of the tubular flexible body further includes:
calculating whether the fluctuation of the position of the first sensor exceeds a first threshold,
calculating whether the fluctuation of the position of the second sensor exceeds a second threshold,
in response to calculating that the fluctuation of the position of the first sensor exceeds the first threshold and calculating that the fluctuation of the position of the second sensor does not exceed the second threshold, setting the position of the distal end of the tubular flexible body to the position of the second sensor, and
in response to calculating that the fluctuation of the position of the first sensor does not exceed the first threshold and calculating that the fluctuation of the position of the second sensor exceeds the second threshold, setting the position of the distal end of the tubular flexible body to the position of the first sensor.

18. The medical system of claim 17, wherein the first threshold is identical to the second threshold.

19. The medical system of claim 16, wherein calculating the position and the orientation of the distal end of the tubular flexible body further includes:
calculating whether the fluctuation of the position of the first sensor exceeds a first threshold,
calculating whether the fluctuation of the position of the second sensor exceeds a second threshold,
in response to calculating that the fluctuation of the position of the first sensor exceeds the first threshold and calculating that the fluctuation of the position of the second sensor does not exceed the second threshold,
weighting the position of the second sensor by increasing a weight of the second sensor based on a difference between the fluctuation of the position of the first sensor and the first threshold,
weighting the position of the first sensor by decreasing a weight of the first sensor based on the difference between the fluctuation of the position of the first sensor and the first threshold, and
calculating the position of the distal end of the tubular flexible body based on the weight of the first sensor, the position of the first sensor, the weight of the second sensor, and the position of the second sensor; and
in response to calculating that the fluctuation of the position of the first sensor does not exceed the first threshold and calculating that the fluctuation of the position of the second sensor exceeds the second threshold,
weighting the position of the first sensor by increasing a weight of the first sensor based on a difference between the fluctuation of the position of the second sensor and the second threshold,
weighting the position of the second sensor by decreasing a weight of the second sensor based on the difference between the fluctuation of the position of the second sensor and the second threshold, and
calculating the position of the distal end of the tubular flexible body based on the weight of the first sensor, the position of the first sensor, the weight of the second sensor, and the position of the second sensor.

20. The medical system of claim 16, wherein calculating the position and the orientation of the distal end of the tubular flexible body further includes:
calculating whether the fluctuation of the orientation of the first sensor exceeds a first threshold,
calculating whether the fluctuation of the orientation of the second sensor exceeds a second threshold,
in response to calculating that the fluctuation of the orientation of the first sensor exceeds the first threshold and calculating that the fluctuation of the orientation of the second sensor does not exceed the second threshold, setting the orientation of the distal end of the tubular flexible body to the orientation of the second sensor, and in response to calculating that the fluctuation of the orientation of the first sensor does not exceed the first threshold and calculating that the fluctuation of the orientation of the second sensor exceeds the second threshold, setting the orientation of the distal end of the tubular flexible body to the orientation of the first sensor.

21. The medical system of claim 16, wherein calculating the position and the orientation of the distal end of the tubular flexible body further includes:

calculating whether the fluctuation of the orientation of the first sensor exceeds a first threshold, calculating whether the fluctuation of the orientation of the second sensor exceeds a second threshold, in response to calculating that the fluctuation of the orientation of the first sensor exceeds the first threshold and calculating that the fluctuation of the orientation of the second sensor does not exceed the second threshold, weighting the orientation of the second sensor by increasing a weight of the second sensor based on a difference between the fluctuation of the orientation of the first sensor and the first threshold, weighting the orientation of the first sensor by decreasing a weight of the first sensor based on the difference between the fluctuation of the orientation of the first sensor and the first threshold, and calculating the orientation of the distal end of the tubular flexible body based on the weight of the first sensor, the orientation of the first sensor, the weight of the second sensor, and the orientation of the second sensor; and in response to calculating that the fluctuation of the orientation of the first sensor does not exceed the first threshold and calculating that the fluctuation of the orientation of the second sensor exceeds the second threshold, weighting the orientation of the first sensor by increasing a weight of the first sensor based on a difference between the fluctuation of the orientation of the second sensor and the second threshold, weighting the orientation of the second sensor by decreasing a weight of the second sensor based on the difference between the fluctuation of the orientation of the second sensor and the second threshold, and calculating the orientation of the distal end of the tubular flexible body based on the weight of the first sensor, the orientation of the first sensor, the weight of the second sensor, and the orientation of the second sensor.

22. The medical system of claim 16, wherein calculating the position and the orientation of the distal end of the tubular flexible body further includes:

calculating whether the fluctuation of the position of the first sensor exceeds a first threshold, calculating whether the fluctuation of the position of the second sensor exceeds a second threshold, in response to calculating that the fluctuation of the position of the first sensor does not exceed the first threshold and calculating that the fluctuation of the position of the second sensor does not exceed the second threshold, setting the position of the distal end of the tubular flexible body to an average of the position of the first sensor and the position of the second sensor.

* * * * *